United States Patent
Johs et al.

(10) Patent No.: US 7,075,649 B1
(45) Date of Patent: Jul. 11, 2006

(54) DISCRETE POLARIZATION STATE ROTATABLE COMPENSATOR SPECTROSCOPIC ELLIPSOMETER SYSTEM, AND METHOD OF CALIBRATION

(75) Inventors: Blaine D. Johs, Lincoln, NE (US); Craig M. Herzinger, Lincoln, NE (US); Steven E. Green, Lincoln, NE (US); Jeffrey S. Hale, Lincoln, NE (US)

(73) Assignee: J.A. Woollam Co., Lincoln, NE (US)

( * ) Notice: Subject to any disclaimer, the term of this patent is extended or adjusted under 35 U.S.C. 154(b) by 675 days.

(21) Appl. No.: 09/945,962

(22) Filed: Sep. 4, 2001

Related U.S. Application Data

(63) Continuation-in-part of application No. 09/517,125, filed on Feb. 29, 2000, now abandoned, and a continuation-in-part of application No. 09/246,888, filed on Feb. 8, 1999, now Pat. No. 6,084,675, which is a continuation-in-part of application No. 08/912,211, filed on Aug. 15, 1997, now Pat. No. 5,872,630, which is a continuation-in-part of application No. 08/530,892, filed on Sep. 20, 1995, now Pat. No. 5,666,201, and a continuation-in-part of application No. 08/618,820, filed on Mar. 20, 1996, now Pat. No. 5,706,212, which is a continuation-in-part of application No. 09/225,118, filed on Jan. 19, 1999, which is a continuation-in-part of application No. 09/223,822, filed on Jan. 19, 1999, which is a continuation-in-part of application No. 09/232,257, filed on Jan. 19, 1999, which is a continuation-in-part of application No. 09/225,371, filed on Jan. 19, 1999, which is a continuation-in-part of application No. 09/225,076, filed on Jan. 19, 1999.

(60) Provisional application No. 60/229,755, filed on Sep. 5, 2000.

(51) Int. Cl.
*G01J 4/00* (2006.01)
(52) U.S. Cl. ...................................... 356/369
(58) Field of Classification Search ........ 356/364–369; 250/225

See application file for complete search history.

(56) References Cited

U.S. PATENT DOCUMENTS 2,700,918 A  2/1955 Osterberg et al.

(Continued)

OTHER PUBLICATIONS

Paper by Johs, titled "Regression Calibration Method for Rotating Element Ellipsometers", Thin Solid Films, 234 (1993).

(Continued)

*Primary Examiner*—Hoa Q. Pham
(74) *Attorney, Agent, or Firm*—James D. Welch

(57) ABSTRACT

Disclosed are spectroscopic ellipsometer and combined spectroscopic reflectometer/ellipsometer systems. The spectroscopic ellipsometer system portion includes polarizer and analyzer elements which remain fixed in position during data acquisition, and a step-wise rotatable compensator electromagnetic beam transmitting means, which serves to enable imposing a plurality of sequentially discrete, rather than continuously varying, polarization states on said beam of electromagnetic radiation. Further disclosed is a calibration procedure for said spectroscopic ellipsometer system portion of the invention which involves the gathering of, for each of a plurality of ellipsometrically distinct sample systems, spectroscopic data at a sequential plurality of discrete electromagnetic radiation beam polarization states, combined with providing of a mathematical model of the spectroscopic ellipsometer system and application of a mathematical regression procedure.

21 Claims, 14 Drawing Sheets

U.S. PATENT DOCUMENTS

| | | | |
|---|---|---|---|
| 3,183,763 A | 5/1965 | Koester | |
| 3,992,104 A | 11/1976 | Watanabe | 356/117 |
| 4,053,232 A | 10/1977 | Dill et al. | 356/118 |
| 4,105,338 A | 8/1978 | Kuroha | 356/118 |
| 4,210,401 A | 7/1980 | Batten | 356/369 |
| 4,332,476 A | 6/1982 | Stenberg et al. | 356/369 |
| 4,355,903 A | 10/1982 | Sandercock | 356/382 |
| 4,373,817 A | 2/1983 | Coates | 356/384 |
| 4,556,292 A | 12/1985 | Mathyssek et al. | 350/394 |
| 4,647,207 A | 3/1987 | Bjork et al. | 356/369 |
| 4,750,822 A | 6/1988 | Rosencwaig et al. | 356/445 |
| 4,826,321 A | 5/1989 | Coates et al. | 356/351 |
| 4,838,695 A | 6/1989 | Mansuripur et al. | 356/369 |
| 5,042,951 A | 8/1991 | Gold et al. | 356/369 |
| 5,045,704 A | 9/1991 | Coates | 356/448 |
| 5,329,357 A | 7/1994 | Bernoux et al. | 356/369 |
| RE34,783 E | 11/1994 | Coates | 250/372 |
| 5,373,359 A | 12/1994 | Woollam et al. | 356/328 |
| 5,475,525 A | 12/1995 | Tournois et al. | 359/245 |
| 5,504,582 A | 4/1996 | Johs et al. | 356/369 |
| 5,521,706 A | 5/1996 | Green et al. | 356/369 |
| 5,581,350 A | 12/1996 | Chen et al. | 356/369 |
| 5,596,411 A | 1/1997 | Fanton et al. | 356/369 |
| 5,608,526 A | 3/1997 | Piwonka-Corle et al. | 356/369 |
| 5,666,201 A | 9/1997 | Johs et al. | 356/369 |
| 5,706,212 A | 1/1998 | Thompson et al. | 364/525 |
| 5,757,494 A | 5/1998 | Green et al. | 356/369 |
| 5,872,630 A | 2/1999 | Johs et al. | 356/369 |
| 5,946,098 A | 8/1999 | Johs et al. | 356/364 |
| 5,956,145 A | 9/1999 | Green et al. | 356/364 |
| 5,963,325 A | 10/1999 | Johs et al. | 356/364 |
| 5,963,327 A | 10/1999 | He et al. | 356/369 |
| 6,084,674 A | 7/2000 | Johs et al. | 356/364 |
| 6,084,675 A | 7/2000 | Herzinger et al. | 356/369 |
| 6,100,981 A | 8/2000 | Johs et al. | 356/364 |
| 6,118,537 A | 9/2000 | Johs et al. | 356/369 |
| 6,141,102 A | 10/2000 | Johs et al. | 356/364 |
| 6,268,917 B1 | 7/2001 | Johs | 356/369 |
| 6,456,376 B1 * | 9/2002 | Liphardt et al. | 356/369 |

OTHER PUBLICATIONS

Paper, by Gottesfeld et al., titled "Combined Ellipsometer and Reflectometer Measurements of Surface Processes on Nobel Metals Electrodes", Surface Sci., 56 (1976).

Paper by Smith, titled "An Automated Scanning Ellipsometer", Surface Science, vol. 56, No. 1. (1976).

Papers, by Azzam and Azzam et al. are also identified as concerning alternative approaches to the goal of the present invention, and are titled.

"Multichannel Polarization State Detectors For Time-Resolved Ellipsometry", Thin Solid Film, 234 (1993); and.

"Spectrophotopolarimeter Based On Multiple Reflections In A Coated Dielectric Slab", Thin Solid Films 313 (1998); and.

"General Analysis And Optimization Of The Four-Detector Photopolarimeter", J. Opt. Soc. Am., A, vol. 5, No. 5 (May 1988); and.

"Accurate Calibration Of Four-Detector Photopolarimeter With Imperfect Polarization Optical Elements", J. Opt. Soc. Am., vol. 6, No. 10, (Oct. 1989).

Review paper by Collins, titled "Automatic Rotating Element Ellipsometers: Calibration, Operation and Real-Time Applications", Rev. Sci. Instrum., 61(8) (1990), is identified for general information.

* cited by examiner

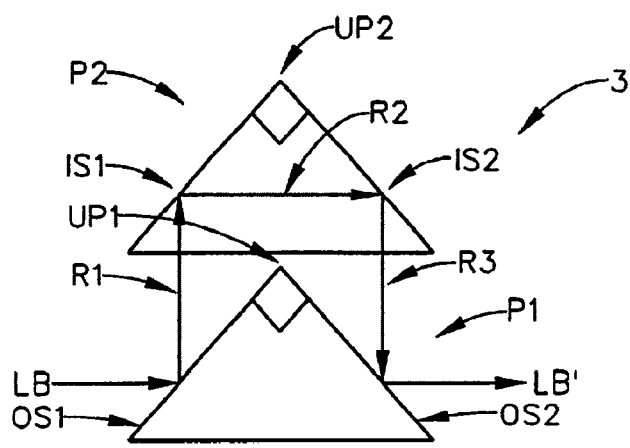
FIG. 3j₁
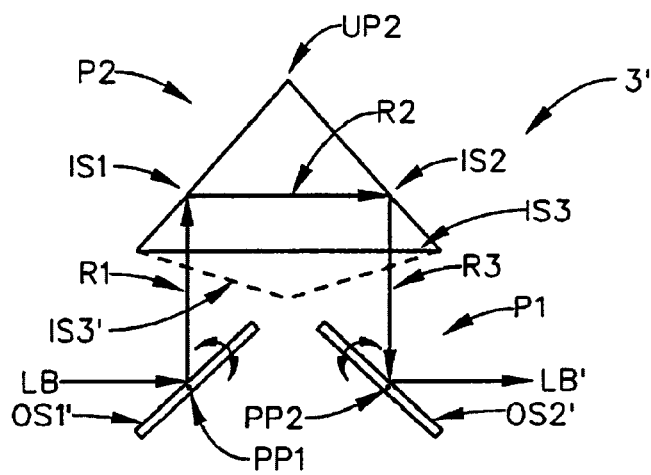
FIG. 3j₂
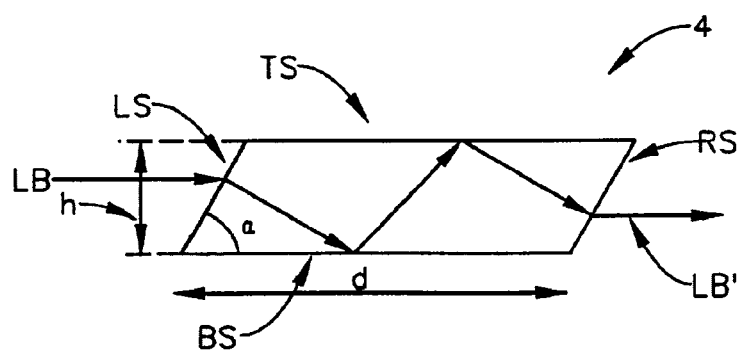
FIG. 3k

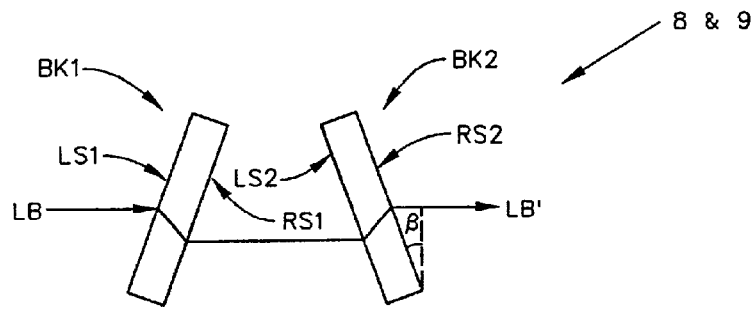
FIG. $3n_1$
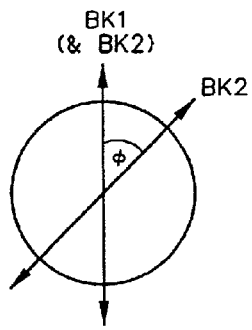
FIG. $3n_2$
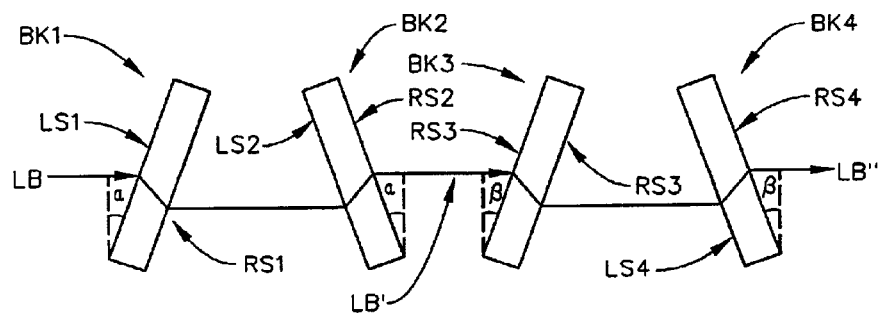
FIG. $3o_1$

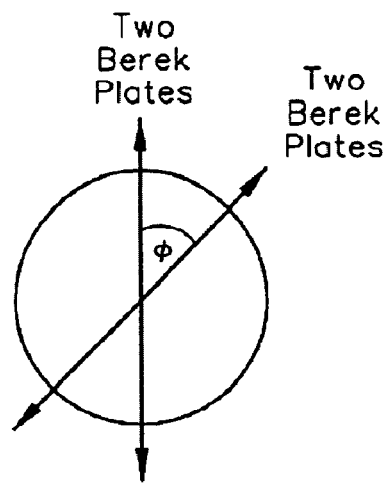
FIG. 3o₂
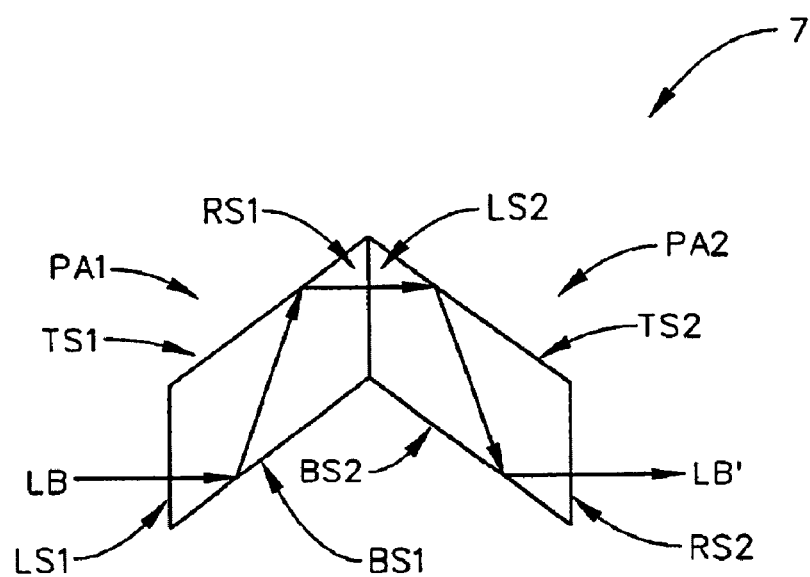
FIG. 3p

Providing a spectroscopic ellipsometer system comprising:
    a source of polychromatic electromagnetic radiation;
    a polarizer which remains fixed in position during data acquisition;
    a stage for supporting a sample system;
    an analyzer which remains fixed in position during data acquisition; and
    a detector system;
said spectroscopic ellipsometer system further comprising at least one means for discretely, sequentially, progressively modifying a polarization state of a beam of electromagnetic radiation provided by said source of polychromatic electromagnetic radiation through a plurality of polarization states, said means being present at at least one location selected from the group consisting of:
    between said polarizer and said stage for supporting a sample system; and
    between said stage for supporting a sample system and said analyzer.

---

For each of at least two ellipsometrically distinguished sample systems, obtaining at least one multi-dimensional data set(s) comprising magnitude as a function of wavelength and a function of a plurality of discrete settings of said at least one means for discretely, sequentially, progressively modifying a polarization state of a beam of electromagnetic radiation provided by said source of polychromatic electromagnetic radiation.

---

Providing a mathematical model of the ellipsometer system, including provision for accounting for the settings of said at least one means for discretely, sequentially, progressively modifying a polarization state of a beam of electromagnetic radiation provided by said source of polychromatic electromagnetic radiation.

---

By simultaneous mathematical regression onto said data sets, evaluating parameters in said mathematical model, including polarization state changing aspects of each of said plurality of discrete settings of said at least one means for discretely, sequentially, progressively modifying a polarization state of a beam of electromagnetic radiation provided by said source of polychromatic electromagnetic radiation.

FIG. 4

DISCRETE POLARIZATION STATE ROTATABLE COMPENSATOR SPECTROSCOPIC ELLIPSOMETER SYSTEM, AND METHOD OF CALIBRATION

This application is a Continuation-In-Part of Provisional Application Ser. No. 60/229,755 filed Sep. 5, 2000. This Application is also a Continuation-in-Part of application Ser. No. 09/517,125 filed Feb. 29, 2000, now abandoned, and of application Ser. No. 09/246,888 filed Feb. 8, 1999 now U.S. Pat. No. 6,084,675. Further, via the Ser. No. 09/246,888 Application, this application is a Continuation-In-Part of application Ser. No. 08/912,211 filed Aug. 15, 1997, (now U.S. Pat. No. 5,872,630), which was a CIP from application Ser. No. 08/530,892 filed Sep. 20, 1995, (now U.S. Pat. No. 5,666,201); and is a CIP of application Ser. No. 08/618,820 filed Mar. 20, 1996, (now U.S. Pat. No. 5,706,212). This Application is further a CIP of Co-Pending application Ser. Nos. 09/225,118; 09/223,822; 09/232,257; 09/225,371; 09/225,076 each filed Jan. 19, 1999 which Applications depend from application Ser. No. 08/997,311 filed Dec. 23, 1997, now U.S. Pat. No. 5,946,098. In addition, priority is Claimed from patent application Ser. No. 09/162,217 filed Sep. 29, 1998.

TECHNICAL FIELD

The present invention relates to ellipsometer and combined reflectometer/ellipsometer systems, as well as methods of calibration therefore. More particularly the present invention comprises, in the ellipsometer portion, provision for providing a sequential plurality of transmissive, stepwise rotated, compensator positions rather than continuously varying, polarization states. The present invention combined spectroscopic reflectometer/ellipsometer system preferably includes system integration via the sharing of a source of spectroscopic electromagnetic radiation and/or the sharing of a spectroscopic multi-element detector system between ellipsometer and reflectometer system portions. The present invention further comprises a calibration procedure for said spectroscopic ellipsometer system which involves the gathering of, for each of a plurality of investigated sample systems, spectroscopic data at a sequential plurality of discrete polarization states.

BACKGROUND

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

In general, modern practice of ellipsometry typically involves causing a spectroscopic beam of electromagnetic radiation, in a known state of polarization, to interact with a sample system at at least one angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system:

$$PSI=|r_p/r_s|; \text{ and}$$

$$DELTA=(\Delta r_p - \Delta r_s).$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

a. a Source of a beam electromagnetic radiation;
    b. a Polarizer element;
    c. optionally a compensator element;
    d. (additional element(s));
    e. a sample system;
    f. (additional element(s));
    g. optionally a compensator element;
    h. an Analyzer element; and
    i. a Spectroscopic Detector System.

Each of said components b.–i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. As described elsewhere in this Specification, the present invention breaks with this convention and provides that no element be continuously rotated during data acquisition but rather that a sequence of discrete polarization states be imposed during data acquisition. This approach allows eliminating many costly components from conventional rotating element ellipsometer systems, and, hence, production of an "Ultra-Low-Cost" ellipsometer system. It is noted, that nulling ellipsometers also exist in which elements therein are rotatable in use, rather than rotating. Generally, use of a nulling ellipsometer system involves imposing a linear polarization state on a beam of electromagnetic radiation with a polarizer, causing the resulting polarized beam of electromagnetic radiation to interact with a sample system, and then adjusting an analyzer to an azimuthal azimuthal angle which effectively cancels out the beam of electromagnetic radiation which proceeds past the sample system. The azimuthal angle of the analyzer at which nulling occurs provides insight to properties of the sample system.

It is further noted that reflectometer systems are generally sequentially comprised of:
- a. a Source of a beam electromagnetic radiation;
- d. (optional additional element(s));
- e. a sample system;
- f. (optional additional element(s));
- i. a Spectroscopic Detector System;

and that reflectometer systems monitor changes in intensity of a beam of electromagnetic radiation caused to interact with a sample system. That is, the ratio of, and phase angle between, orthogonal components in a polarized beam are not of direct concern.

Continuing, in use, data sets can be obtained with an ellipsometer system configured with a sample system present, sequentially for cases where other sample systems are present, and where an ellipsometer system is configured in a straight-through configuration wherein a beam of electromagnetic radiation is caused to pass straight through the ellipsometer system without interacting with a sample system. Simultaneous mathematical regression utilizing multiple data sets can allow evaluation of sample system characterizing PSI and DELTA values over a range of wavelengths. The obtaining of numerous data sets with an ellipsometer system configured with, for instance, a sequence of sample systems present and/or wherein a sequential plurality of polarization states are imposed on an electromagnetic beam caused to interact therewith, can allow system calibration of numerous ellipsometer system variables.

Patents of which the Inventor is aware include those to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to ellipsometer systems.

Further Patents of which the Inventor is aware include U.S. Pat. Nos. 5,757,494 and 5,956,145 to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said Patents describes the presence of a variable, transmissive, bi-refringent component which is added, and the application thereof during data acquisition to enable the identified capability.

A Patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein.

A Patent to He et al., U.S. Pat. No. 5,963,327 is disclosed as it describes an ellipsometer system which enables providing a polarized beam of electromagnetic radiation at an oblique angle-of-incidence to a sample system in a small spot area.

A Patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

Patent to Dill et al., U.S. Pat. No. 4,953,232 is disclosed as it describes a rotating compensator ellipsometer system.

Patents co-owned with this Application, which Patents Claim various Compensator Designs recited in Claims herein, and which Patents are incorporated hereinto by reference are:
- U.S. Pat. No. 5,946,098 to Johs et al.;
- U.S. Pat. No. 5,963,325 to Johs et al.;
- U.S. Pat. No. 6,084,674 to Johs et al.;
- U.S. Pat. No. 6,084,675 to Herzinger et al.;
- U.S. Pat. No. 6,100,981 to Johs et al.;
- U.S. Pat. No. 6,118,537 to Johs et al.;
- U.S. Pat. No. 6,141,102 to Johs et al.

Patents cited in examination of said Patents included No. 4,556,292 to Mathyssek et al. and U.S. Pat. No. 5,475,525 to Tournois et al.

A Patent to Coates et al., U.S. Pat. No. 4,826,321 is disclosed as it describes applying a reflected monochromatic beam of plane polarized electromagnetic radiation at a Brewster angle of incidence to a sample substrate to determine the thickness of a thin film thereupon. This Patent also describes calibration utilizing two sample substrates, which have different depths of surface coating.

Other Patents which describe use of reflected electromagnetic radiation to investigate sample systems are No. RE 34,783, U.S. Pat. Nos. 4,373,817, and 5,045,704 to Coates; and U.S. Pat. No. 5,452,091 to Johnson.

A Patent to Bjork et al., U.S. Pat. No. 4,647,207 is disclosed as it describes an ellipsometer system which has provision for sequentially positioning a plurality of reflective polarization state modifiers in a beam of electromagnetic radiation. While said 207 Patent mentions investigating a sample system in a transmission mode, no mention or suggestion is found for utilizing a plurality of transmitting polarization state modifiers, emphasis added. U.S. Pat. Nos. 4,210,401; 4,332,476 and 4,355,903 are also identified as being cited in the 207 Patent. It is noted that systems as disclosed in these Patents, (particularly in the 476 Patent), which utilize reflection from an element to modify a polarization state can, that if such an element is an essential duplicate of an investigated sample and is rotated ninety degrees therefrom, then the effect of the polarization state modifying element on the electromagnetic beam effect is extinguished by the sample.

A Patent to Mansuripur et al., U.S. Pat. No. 4,838,695 is disclosed as it describes an apparatus for measuring reflectivity.

Patents to Rosencwaig et al., U.S. Pat. Nos. 4,750,822 and 5,595,406 are also identified as they describe systems which impinge electromagnetic beams onto sample systems at oblique angles of incidence. The 406 Patent provides for use of multiple wavelengths and multiple angles of incidence. For similar reasons U.S. Pat. No. 5,042,951 to Gold et al. is also disclosed.

A Patent to Osterberg, U.S. Pat. No. 2,700,918 describes a microscope with variable means for increasing the visibility of optical images, partially comprised of discrete bi-refringent plates which can be positioned in the pathway between an eyepiece and an observed object. Other Patents identified in a Search which identified said 918 Patent are U.S. Pat. No. 3,183,763 to Koester; No. 4,105,338 to Kuroha; U.S. Pat. No. 3,992,104 to Watanabe and a Russian Patent, No. SU 1518728. Said other Patents are not believed to be particularly relevant, however.

A Patent, U.S. Pat. No. 5,329,357 to Bernoux et al. is also identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this Patent is not controlling where electromagnetic radiation carrying fiber optics are present.

A Patent to Chen et al., U.S. Pat. No. 5,581,350, is disclosed as it describes a method for regression calibration of ellipsometers.

As present invention preferred practice is to utilize a spectroscopic source of electromagnetic radiation with a relatively flat spectrum over a large range of wavelengths Patent U.S. Pat. No. 6,628,917 to Johs is disclosed. Patents relevant thereto include U.S. Pat. No. 5,179,462 to Kageyama et al. is identified as it provides a sequence of three electromagnetic beam combining dichroic mirrors in an arrangement which produces an output beam of electromagnetic radiation that contains wavelengths from each of four sources of electromagnetic radiation. Each electromagnetic beam combining dichroic mirror is arranged so as to transmit a first input beam of electromagnetic radiation, comprising at least a first wavelength content, therethrough so that it exits a second side of said electromagnetic beam combining dichroic mirror, and to reflect a second beam of electromagnetic radiation, comprising an additional wavelength content, from said second side of said electromagnetic beam combining dichroic mirror in a manner that a single output beam of electromagnetic radiation is formed which contains the wavelength content of both sources of electromagnetic radiation. The sources of electromagnetic radiation are described as lasers in said 462 Patent. Another Patent, U.S. Pat. No. 5,296,958 to Roddy et al., describes a similar system which utilizes Thompson Prisms to similarly combine electromagnetic beams for laser source. U.S. Pat. Nos. 4,982,206 and 5,113,279 to Kessler et al. and Hanamoto et al. respectively, describe similar electromagnetic electromagnetic beam combination systems in laser printer and laser beam scanning systems respectively. Another Patent, U.S. Pat. No. 3,947,688 to Massey, describes a method of generating tuneable coherent ultraviolet light, comprising use of an electromagnetic electromagnetic beam combining system. A Patent to Miller et al., U.S. Pat. No. 5,155,623, describes a system for combining information beams in which a mirror comprising alternating regions of transparent and reflecting regions is utilized to combine transmitted and reflected beams of electromagnetic radiation into a single output beam. A Patent to Wright, U.S. Pat. No. 5,002,371 is also mentioned as describing a beam splitter system which operates to separate "P" and "S" orthogonal components in a beam of polarized electromagnetic radiation.

In addition to the identified Patents, certain Scientific papers are also identified.

A paper by Johs, titled "Regression Calibration Method for Rotating Element Ellipsometers", Thin Solid Films, 234 (1993) is also disclosed as it describes a mathematical regression based approach to calibrating ellipsometer systems.

Another paper, by Gottesfeld et al., titled "Combined Ellipsometer and Reflectometer Measurements of Surface Processes on Nobel Metals Electrodes", Surface Sci., 56 (1976), is also identified as describing the benefits of combining ellipsometry and reflectometry.

A paper by Smith, titled "An Automated Scanning Ellipsometer", Surface Science, Vol. 56, U.S. Pat. No. 1. (1976), is also mentioned as it describes an ellipsometer system which does not require any moving, (eg. rotating), elements during data acquisition.

Four additional papers by Azzam and Azzam et al. are also identified and are titled:

"Multichannel Polarization State Detectors For Time-Resolved Ellipsometry", Thin Solid Film, 234 (1993); and "Spectrophotopolarimeter Based On Multiple Reflections In A Coated Dielectric Slab", Thin Solid Films 313 (1998); and "General Analysis And Optimization Of The Four-Detector Photopolarimeter", J. Opt. Soc. Am., A, Vol. 5, No. 5 (May 1988); and "Accurate Calibration Of Four-Detector Photopolarimeter With Imperfect Polarization Optical Elements", J. Opt. Soc. Am., Vol. 6, No. 10, (October 1989);

as they describe alternative approaches concerning the goal of the present invention.

Even in view of relevant prior art, there remains need for a spectroscopic ellipsometer system which:

presents with stationary polarizer and analyzer during data acquisition; and utilizes a plurality of transmissive step-wise rotatable compensator means to effect a plurality of sequential discrete, rather than continuously varying, polarization states during said data acquisition; and which allows optional integrated combination with a reflectometer system via the sharing of a source of spectroscopic electromagnetic radiation and/or a spectroscopic multi-element detector system therewith.

In addition there remains need for a calibration procedure for a spectroscopic ellipsometer system which involves the gathering of spectroscopic data at a plurality of discrete polarization states for each of some number of sample systems. The present invention responds to said identified needs.

DISCLOSURE OF THE INVENTION

The present invention is, in the first instance, a spectroscopic ellipsometer system basically comprising:

a source of polychromatic electromagnetic radiation;

a polarizer which is fixed in position during data acquisition;

a stage for supporting a sample system;

an analyzer which is fixed in position during data acquisition; and a multi-element spectroscopic detector system.

In addition, the present invention ellipsometer system further comprises at least one means for discretely, sequentially, modifying a polarization state of a beam of electromagnetic radiation through a plurality of polarization states. The at least one means for discretely, sequentially, modifying a polarization state of a beam of electromagnetic radiation through a plurality of polarization states, is positioned between said polarizer and said stage for supporting a sample system, and/or and between said stage for supporting a sample system and said analyzer, and so that said beam of electromagnetic radiation transmits through a polarization state modifier element thereof in use. The present invention at least one means for discretely, sequentially, modifying a polarization state of a beam of electromagnetic radiation through a plurality of polarization states comprises a compensator which is mounted to allow step-wise rotation about the locus of a beam of electromagentic radiation caused to pass therethrough.

The present invention is further a combination spectroscopic reflectometer/ellipsometer system basically comprising:

a source of polychromatic electromagnetic radiation;

a stage for supporting a sample system;

a multi-element spectroscopic detector system.

The combination spectroscopic reflectometer/ellipsometer system further comprises, in the ellipsometer system portion thereof, a polarizer, (which is fixed in position during data acquisition), present between the source of polychromatic electromagnetic radiation and the stage for supporting a sample system, and an analyzer, (which is fixed in position during data acquisition), present between the stage for supporting a sample system and the multi-element spectroscopic detector system. The ellipsometer system also comprises at least one means for discretely, sequentially, modifying a polarization state of a beam of electromagnetic radiation through a plurality of polarization states present between said polarizer and said stage for supporting a sample system, and/or between said stage for supporting a sample system and said analyzer, and positioned so that said beam of electromagnetic radiation transmits through a polarization state modifier element therein during use.

Additionally, the combination spectroscopic reflectometer/ellipsometer system is configured such that a polychromatic beam of electromagnetic radiation provided by said source of polychromatic electromagnetic radiation can, optionally, be directed to interact with a sample system present on said stage for supporting a sample system without any polarization state being imposed thereupon, and such that a polychromatic beam of electromagnetic radiation also provided by said source of polychromatic electromagnetic radiation can be, optionally simultaneously, directed to interact with a sample system present on said stage for supporting a sample system after a polarization state has been imposed thereupon. The polychromatic beam of electromagnetic radiation without any polarization state imposed thereupon, when directed to interact with a sample system present on said stage for supporting a sample system, is typically caused to approach said sample system at an oblique angle-of-incidence which is between a sample system Brewster angle and a normal to the surface of the sample system. Further, the polychromatic beam of electromagnetic radiation provided by said source of polychromatic electromagnetic radiation upon which a polarization state has been imposed, is typically directed to interact with a sample system present on said stage for supporting a sample system at an angle near the Brewster angle of the sample system being investigated. Either, or both, the polychromatic beam(s) of electromagnetic radiation provided by said source of polychromatic electromagnetic radiation, upon which is imposed a polarization state or upon which no polarization state is imposed, is preferably directed to interact with a sample system present on said stage for supporting a sample system via a fiber optic means.

While the present invention can utilize essentially any Compensator, a preferred embodiment of the present invention provides that at least one of said at least one compensator(s), which is mounted to allow step-wise rotation about the locus of a beam of electromagentic radiation caused to pass therethrough, be selected from the group consisting of:

a single element compensator;

a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

where the identifiers are shown in FIGS. 3e–3i.

Additional compensator systems, previously disclosed in patent application Ser. No. 08/997,311, (now U.S. Pat. No. 5,946,098), and CIP's therefrom, which are specifically within the scope of the invention and can be included in the selection group are:

a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation.

It is to be appreciated that the present Application does not apply Compensator(s) in a system which causes continuous rotation thereof during data acquisition, but rather steps a compensator through a series of discrete rotational positions, and holds it stationary while obtaining data. Further, while not required, the present invention benefits from Compensator(s) designed to provide relatively constant, achromatic Polarization State Modification effects over a Spectroscopic range of wavelengths.

As another previously disclosed, (in Co-Pending application Ser. No. 09/517,125), non-limiting example, the spectroscopic ellipsometer system can provide at least one means for discretely, sequentially, modifying a polarization state of a beam of electromagnetic radiation provided by said source of polychromatic electromagnetic radiation through a plurality of polarization states, can comprise an essentially circular "wheel" element with a plurality of discrete polarization state modifier elements mounted thereupon, on the perimeter thereof, and projecting perpendicularly to a surface of said essentially circular "wheel". The essentially circular "wheel" element further comprises a means for causing rotation about a normal to said surface thereof, such that in use said essentially circular "wheel" element is caused to rotate to position a discrete polarization state modifier element such that the beam of electromagnetic radiation, provided by said source of polychromatic electromagnetic radiation, passes therethrough.

As another previously disclosed, (in Co-Pending application Ser. No. 09/517,125), non-limiting example, the spectroscopic ellipsometer system at least one means for discretely, sequentially, modifying a polarization state of a beam of electromagnetic radiation provided by said source of polychromatic electromagnetic radiation through a plurality of polarization states, can comprise a plurality of discrete polarization state modifier elements mounted on a slider element which is mounted in a guide providing element. During use sliding the slider element to the right or left serves to position a discrete polarizer element such that said a beam of electromagnetic radiation, provided by said source of polychromatic electromagnetic radiation, passes therethrough.

Continuing, again as previously disclosed, (in application Ser. No. 09/517,125, now U.S. Pat. No. 6,268,917), it is further noted that a system for providing an output beam of polychromatic electromagnetic radiation which has a relatively broad and flattened Intensity vs. Wavelength characteristic over a wavelength spectrum for use in said present invention systems can be applied in the present invention system. The reason for doing so is to provide an output beam of polychromatic electromagnetic radiation which is substantially a comingled composite of a plurality of input beams of polychromatic electromagnetic radiation which individually do not provide as relatively broad and flattened a intensity vs. wavelength characteristic over said wavelength spectrum, as does said output comingled composite beam of polychromatic electromagnetic radiation. The system for providing an output beam of polychromatic electromagnetic radiation, which has a relatively broad and flattened intensity vs. wavelength characteristic over a wavelength spectrum, comprises:

a. at least a first and a second source of polychromatic electromagnetic radiation; and
  b. at least a first electromagnetic beam combining means comprising a plate, (eg. uncoated fused silica or glass etc. such that transmission characteristics thereof are determined by angle-of-incidence and polarization state of a beam of electromagnetic radiation).

The at least a first electromagnetic beam combining means is positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means. The resultant beam of polychromatic electromagnetic radiation exiting the first electromagnetic beam combining means is substantially an output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

Said system for providing an output beam of polychromatic electromagnetic radiation which has a relatively broad and flattened intensity vs. wavelength characteristic over a wavelength spectrum can also be optionally further characterized by a third source of polychromatic electromagnetic radiation, and/or a second electromagnetic beam combining (BCM) means comprising an uncoated plate, (eg. fused silica or glass etc. such that transmission characteristics thereof are determined by angle-of-incidence and polarization state of a beam of electromagnetic radiation). The second electromagnetic beam combining means, when present, is positioned with respect to said comingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means. The second electromagnetic beam combining means is also positioned with respect to the third source of polychromatic electromagnetic radiation, (when present), such that a beam of electromagnetic radiation from said third source of polychromatic electromagnetic radiation reflects from said second electromagnetic beam combining means, such that a second resultant beam of polychromatic electromagnetic radiation which is substantially an output beam of polychromatic electromagnetic radiation which has a relatively even more broadened and flattened intensity vs. wavelength over a wavelength spectrum, comprising said comingled composite of a plurality of input beams of polychromatic electromagnetic radiation from said first, second and third sources, which first, second and third sources individually do not provide such a relatively even more broadened and flattened intensity vs. wavelength over a wavelength spectrum characteristic.

At least one of said first and second, (when present), electromagnetic beam combining means can be pivotally mounted such that, for instance, the angle at which a beam of polychromatic electromagnetic radiation from the second source of polychromatic electromagnetic radiation reflects from the at least one electromagnetic beam combining means can be controlled to place it coincident with the locus of a beam of polychromatic electromagnetic radiation transmitted therethrough. Pivot means providing two dimensional degrees of rotation freedom are preferred in this application. Further, where sources of polychromatic electromagnetic radiation can be moved, the pivot capability can be utilized to allow use of optimum tilts of electromagnetic beam combining means. That is, transmission and reflection characteristics of an electromagnetic beam combining means vary with the angle of incidence a transmitted or reflected bear makes with respect thereto, and pivot means can allow adjusting tilt to optimize said characteristics.

Further, as the polarizer in the present invention spectroscopic ellipsometer system remains essentially fixed in position during data acquisition, it is noted that it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between "S" polarization transmission and reflection components is less, as a function of wavelength and electromagnetic beam angle-of-incidence to said beam combining means, when compared to that of the "P" components. The "P" component is far more affected, particularly around a Brewster angle condition, hence, where an "S" component, with reference to a beam combining system, is utilized, it is to be appreciated that variation in intensity of transmitted and reflected beams of electromagnetic radiation output from the beam combining system, as functions of wavelength and the angles of incidence of beams of electromagnetic radiation from sources of said transmitted and reflected beams of electromagnetic radiation, is minimized, as compared to variation which occurs in "P" components.

Before discussing the Method of Calibration of the present invention spectroscopic ellipsometer system, it is noted that the polarizer and analyzer thereof, which are essentially fixed in position during data acquisition, are not necessarily absolutely fixed in position. Said polarizer and analyzer are preferably what is properly termed "Rotatable". That is they can be rotated to various positions by a user between data acquisitions, but they are not caused to be Rotating while data is being acquired, (Typical positioning of analyzer and polarizer azimuthal angles are plus or minus forty-five (+/−45) degrees).

Continuing, a present invention method of calibrating a spectroscopic ellipsometer system comprising the steps of:

a. providing a spectroscopic ellipsometer system as described above herein, either independently or in functional combination with a reflectometer system;

said method further comprising, in any functional order, the steps of:

b. for each of at least two ellipsometrically different sample systems, obtaining at least one multi-dimensional data set(s) comprising intensity as a function of wavelength and a function of a plurality of discrete settings of said at least one means for discretely, sequentially, modifying a polarization state of a beam of electromagnetic radiation provided by said source of polychromatic electromagnetic radiation;

c. providing a mathematical model of the ellipsometer system, including provision for accounting for the settings of said at least one means for discretely, sequentially, modifying a polarization state of a beam of electromagnetic radiation provided by said source of polychromatic electromagnetic radiation utilized in step b; and d. by simultaneous mathematical regression onto said data sets, evaluating parameters in said mathematical model, including polarization state changing aspects of each of said plurality of discrete settings of said at least one means for discretely, sequentially, modifying a polarization state of a beam of electromagnetic radiation provided by said source of polychromatic electromagnetic radiation.

It is also mentioned that said method of calibrating a spectroscopic ellipsometer system can require, in the step b. obtaining of at least one multi-dimensional data set(s) comprising intensity as a function of wavelength and a function of a plurality of discrete settings of said at least one means for discretely, sequentially, modifying a polarization state of a beam of electromagnetic radiation, the obtaining of data from at least as many sample systems as are utilized discrete settings of said at least one means for discretely, sequentially, modifying a polarization state of a beam of electromagnetic radiation provided by said source of polychromatic electromagnetic radiation. However, if characteristics of a means for discretely, sequentially, modifying a polarization state of a beam of electromagnetic radiation are parameterized, say as a function of wavelength, are expressed by equations with a minimized number of parameters therein, it is possible to reduce the number of sample systems which must be utilized.

The preferred embodiment of the present invention involves positioning input and output polarizer/analyzer system azimuthal angles at typical fixed, nominal, constant plus or minus forty-five (+/−45) degrees, although use of polarizer and analyzer elements which are rotatable between data acquisition procedures is acceptable. It is noted that the static positioning of said input and output polarizer/analyzer system azimuthal angles greatly simplifies data acquisition, in that no phase sensors are required to detect rotational positioning are necessary, because synchronization is unnecessary. That is, as ellipsometric data is acquired asynchronously, the system requirements are greatly reduced as compared to ellipsometer systems which involve elements that are caused to rotate during data acquisition. Also, as alluded to, fiber optics are the preferred via for transporting electromagnetic radiation to and from the ellipsometer system portion of the present invention. The foregoing points make it possible to retro-fit mount the ellipsometer portion of the present invention to existing spectroscopic reflectometer systems, (such as those presently marketed by Nanometrics Inc.), in a manner that optionally involves sharing of a source of electromagnetic radiation and/or detector system thereof with said ellipsometer system.

While the foregoing has disclosed the present invention system, it remains to describe the mathematical basis for practicing the present invention. As described, the present Discrete Polarization State Spectroscopic Ellipsometer (DSP-SE$_{tm}$) system basically consists of a source of polychromatic electromagnetic radiation, an optical element for setting a polarization state, (eg. a polarizer), a stage for supporting a sample system with a sample system present thereupon, a means for discretely, sequentially, modifying a polarization state of a beam of electromagnetic radiation provided by said source of polychromatic electromagnetic radiation through a plurality of polarization states by passage therethrough, an analyzer, and a means for detecting beam intensity, (eg. a detector system). As indicated, in practice the input element is typically a polarizer with its transmission axis oriented approximately +45 or −45 degrees from the sample system plane of incidence. Using Mueller Matrix/Stokes Vector Calculus, the input beam passing through such a polarizer is represented by:

$$I_P = \begin{pmatrix} 1 \\ \cos(2P) \\ \sin(2P) \\ 0 \end{pmatrix}$$

where "P" is the azimuthal angle of the polarizer with respect to the sample plane of incidence. For optimal performance over a wide range of sample systems, and computational simplicity, the "P" is usually chosen to be +/−45 degrees, and the Stokes Vector becomes:

$$I_P = \begin{pmatrix} 1 \\ 0 \\ \pm 1 \\ 0 \end{pmatrix}$$

Now, an isotropic sample can be optically modeled by the Mueller Matrix:

$$M_S = \begin{pmatrix} 1 & -N & 0 & 0 \\ -N & 1 & 0 & 0 \\ 0 & 0 & C & S \\ 0 & 0 & -S & C \end{pmatrix}$$

and the Stokes Vector resulting from a polarized polychromatic electromagnetic radiation beam interaction with a sample system is described by:

$$M_S \cdot I_P = \begin{pmatrix} 1 & -N & 0 & 0 \\ -N & 1 & 0 & 0 \\ 0 & 0 & C & S \\ 0 & 0 & -S & C \end{pmatrix} \cdot \begin{pmatrix} 1 \\ 0 \\ \pm 1 \\ 0 \end{pmatrix} = \begin{pmatrix} 1 \\ -N \\ C \cdot \pm 1 \\ -S \cdot \pm 1 \end{pmatrix}$$

A generalized polarization state modifier (PSM) element, (which can comrpise a combination of elements), followed by a polarization state insensitive detector yields the following Stokes Vector:

$$PSM = (1\ 0\ 0\ 0) \cdot \begin{pmatrix} m00 & m01 & m02 & m03 \\ m10 & m11 & m12 & m13 \\ m20 & m21 & m22 & m23 \\ m30 & m31 & m32 & m33 \end{pmatrix}$$
$$= (m00\ m01\ m02\ m03)$$

therefore, if there are "n" discrete polarization states, the beam intensity measured for the "n'th" polarization state is:

$$I_n = PSM_n \cdot M_S \cdot I_P = (m0_n\ m1_n\ m2_n\ m3_m) \cdot$$
$$\begin{pmatrix} 1 & -N & 0 & 0 \\ -N & 1 & 0 & 0 \\ 0 & 0 & C & S \\ 0 & 0 & -S & C \end{pmatrix} \begin{pmatrix} 1 \\ 0 \\ \pm 1 \\ 0 \end{pmatrix}$$
$$= m0_n - m1_n \cdot N + (m2_n \cdot C - m3_m \cdot S) \cdot \pm 1$$

The transfer matrix for traditional 4-detector polarimeter systems is constructed by inserting the (PSM) into "rows" which correspond to the polarization state measured by each detector:

$$I_n = A \cdot S \begin{pmatrix} I_0 \\ I_1 \\ I_2 \\ I_3 \end{pmatrix} = \begin{pmatrix} m0_0 & m1_0 & m2_0 & m3_0 \\ m0_1 & m1_1 & m2_1 & m3_1 \\ m0_2 & m1_2 & m2_2 & m3_2 \\ m0_3 & m1_3 & m2_3 & m3_3 \end{pmatrix} \cdot \begin{pmatrix} 1 \\ -N \\ C \cdot \pm 1 \\ -S \cdot \pm 1 \end{pmatrix}$$

If the "A" transfer matrix is invertable, (ie. the determinate is non-zero), it can be concluded that sample system's N, C and S ellipsometric parameters can be determined from the measured intensities at each detector.

$$\begin{pmatrix} 1 \\ -N \\ C \cdot \pm 1 \\ -S \cdot \pm 1 \end{pmatrix} = A^{-1} \cdot \begin{pmatrix} I_0 \\ I_1 \\ I_2 \\ I_3 \end{pmatrix}$$

Furthermore, in a traditional 4-detector polarimeter system, the "A" transfer matrix is determined, (at each wavelength of operation), by inputting a series of known polarization states and measuring the resulting intensities at each detector.

While the present invention (DSP-SE$_{tm}$) is similar to traditional 4-detector polarimeter systems, if differs in that more than 4 polarization states can optionally be incorporated into the measurement. The "A" matric therefore is generally not "square", and a simple inversion can not be used to directly extract sample system N, C and S ellipsometic parameters. Regression analysis based on known optical models can also be used to determine, (ie. calibrate), the "A" transfer matrix of the system, and to extract the ellipsometric parameters from the "n" measuremed intensities.

While many variations are possible, in the preferred, non-limiting, embodiment of the present invention the (DSP-SE$_{tm}$) the input polarizer, as mentioned, is fixed at 45 degrees, such that the Stokes Vector which enters the polarimeter after interaction with the sample system is given by:

$$M_S \cdot I_P = k \cdot \begin{pmatrix} 1 & -N & 0 & 0 \\ -N & 1 & 0 & 0 \\ 0 & 0 & C & S \\ 0 & 0 & -S & C \end{pmatrix} \begin{pmatrix} 1 \\ 0 \\ 1 \\ 0 \end{pmatrix} = k \cdot \begin{pmatrix} 1 \\ -N \\ C \\ -S \end{pmatrix}$$

(where "k" is an arbitrary constant which accounts for the unknown intensity provided by the source of polychromatic electromagnetic radiation).

For the 1st discrete polarization state of the detector system, a polarizer, (typically termed an analyzer when placed after the sample system), with the azimuthal angle threof set at 45 degrees, the detected intensity is of the form:

$$I_0 = PSM_0 \cdot M_S \cdot I_P = (1 \ 0 \ -1 \ 0) \cdot k \cdot \begin{pmatrix} 1 \\ -N \\ C \\ -S \end{pmatrix} = k \cdot (1 - C)$$

For the next two discrete polarization states, a quarter-wave retarder can be inserted in front of the analyzer, at azimuthal angles of zero (0.0) and ninety (90) degrees respectively, to provide:

$$I_1 =$$

$$PSM_1 \cdot M_S \cdot I_P = (1 \ 0 \ -1 \ 0) \cdot \begin{pmatrix} 1 & 0 & 0 & 0 \\ 0 & 1 & 0 & 0 \\ 0 & 0 & 0 & 1 \\ 0 & 0 & -1 & 0 \end{pmatrix} \cdot k \cdot \begin{pmatrix} 1 \\ -N \\ C \\ -S \end{pmatrix} = k \cdot (1 + S)$$

-continued (for retarder@0°)

$$I_2 =$$

$$PSM_2 \cdot M_S \cdot I_P = (1 \ 0 \ -1 \ 0) \cdot \begin{pmatrix} 1 & 0 & 0 & 0 \\ 0 & 1 & 0 & 0 \\ 0 & 0 & 0 & -1 \\ 0 & 0 & 1 & 0 \end{pmatrix} \cdot k \cdot \begin{pmatrix} 1 \\ -N \\ C \\ -S \end{pmatrix} = k \cdot (1 - S)$$

(for retarder@90°)

For two additional discrete polarization states, a quarter-wave retarder can be inserted in front of the analyzer, at azimuthal angles of +/- twenty-two (22) degrees, respectively, to provide:

$$I_3 = PSM_3 \cdot M_S \cdot I_P =$$

$$(1 \ 0 \ -1 \ 0) \cdot \begin{pmatrix} 1 & 0 & 0 & 0 \\ 0 & \frac{1}{2} & \frac{1}{2} & \frac{-1}{2} \cdot \sqrt{2} \\ 0 & \frac{1}{2} & \frac{1}{2} & \frac{1}{2} \cdot \sqrt{2} \\ 0 & \frac{1}{2} \cdot \sqrt{2} & \frac{-1}{2} \cdot \sqrt{2} & 0 \end{pmatrix} \cdot k \cdot \begin{pmatrix} 1 \\ -N \\ C \\ -S \end{pmatrix} =$$

$$\left(1 - \frac{1}{2} \cdot C + \frac{1}{2} \cdot N + \frac{1}{2} \cdot \sqrt{2} \cdot S\right) \cdot k$$

(for retarder@+22.5°)

$$I_4 = PSM_4 \cdot M_S \cdot I_P = (1 \ 0 \ -1 \ 0) \cdot$$

$$\begin{pmatrix} 1 & 0 & 0 & 0 \\ 0 & \frac{1}{2} & \frac{-1}{2} & \frac{1}{2} \cdot \sqrt{2} \\ 0 & \frac{-1}{2} & \frac{1}{2} & \frac{1}{2} \cdot \sqrt{2} \\ 0 & \frac{-1}{2} \cdot \sqrt{2} & \frac{-1}{2} \cdot \sqrt{2} & 0 \end{pmatrix} \cdot k \cdot \begin{pmatrix} 1 \\ -N \\ C \\ -S \end{pmatrix}$$

$$= \left(1 + \frac{1}{2} \cdot \sqrt{2} \cdot S - \frac{1}{2} \cdot N - \frac{1}{2} \cdot C\right) \cdot k$$

(for retarder@-22.5')

Simple combinations of these intensities yield:

$$I_0 = k(1-C)$$

$$I_1 - I_2 = 2 \cdot k \cdot S$$

$$I_1 + I_2 = 2 \cdot k$$

$$I_3 - I_4 = k \cdot N$$

from which sample system N, C, S, and are easily derived as:

$$N = 2 \cdot \frac{I_3 - I_4}{I_1 + I_2}$$

$$C = \frac{(I_1 + I_2 - 2 \cdot I_0)}{(I_1 + I_2)}$$

-continued $$S = \frac{(I_1 - I_2)}{(I_1 + I_2)}$$

$$\Delta = \mathrm{atan}\left(\frac{S}{C}\right)$$

$$\Psi = \frac{1}{2} \cdot \mathrm{atan}\left(\frac{\sqrt{C^2 + S^2}}{N}\right)$$

While the math for the preceeding 5-state (DSP-SE$_{tm}$) system is elegant, a potential difficulty in implementing said design is that insertion of the quarter-wave plates to effect polarization states 1–4, introduces intensity loss as a result of reflection from the optical element surface, which is not present when obtaining the first data set wherein no quarter-wave plate is present. This additional intensity loss must be accounted for in the calibration algorithm. A modified approach involves not obtaining or not utilizing the first data set. While this slightly complicates the equations, a simple analytic solution is still possible and values for N, C and S can be derrived as:

$$I_1 - I_2 = 2 \cdot k \cdot S$$

$$I_1 + I_2 = 2 \cdot k$$

$$I_3 - I_4 = k \cdot N$$

$$I_3 + I_4 = (2 - C + \sqrt{2} \cdot S) \cdot k$$

$$N = 2 \cdot \frac{I_3 - I_4}{I_1 + I_2}$$

$$C = \frac{(2 - \sqrt{2}) \cdot I_2 + (2 + \sqrt{2}) \cdot I_1 - 2 \cdot (I_3 + I_4)}{(I_1 + I_2)}$$

$$S = \frac{(I_1 - I_2)}{(I_1 + I_2)}$$

A more general 4-state (DSP-SE$_{tm}$) approach utilizes an input polarizer, an output analyzer and four (4) retarder elements at various azimuthal orientations. In this approach while the azimuthal orientations for the optical elements are nominally chosen to be the same as in the preceeding design, arbitrary azimuthal orientations as well as non-ninety degree retardation values are allowed. Under this approach, the Stokes Vector provided to the Polarimeter is given by:

$$I_{S,P} = \begin{pmatrix} 1 & -N & 0 & 0 \\ -N & 1 & 0 & 0 \\ 0 & 0 & C & S \\ 0 & 0 & -S & C \end{pmatrix} \cdot \begin{pmatrix} 1 \\ \cos(2P) \\ \sin(2P) \\ 0 \end{pmatrix} \quad \text{(DPS \#1)}$$

$$= \begin{pmatrix} 1 - N \cdot \cos(2 \cdot P) \\ -N + \cos(2 \cdot P) \\ C \cdot \sin(2 \cdot P) \\ -S \cdot \sin(2 \cdot P) \end{pmatrix} = \begin{pmatrix} s0 \\ s1 \\ s2 \\ s3 \end{pmatrix}$$

(where "P" is the input polarimeter azimuth).

The response of each discrete polarization state "n" to an input Stokes Vector is:

$$I_n = (m0_n \ m1_n \ m2_n \ m3_n) \quad \text{(DPS \#2)}$$

$$m0_n = 1$$

$$m1_n = (cr_n \cdot sr_n - c\delta_n \cdot sr_n \cdot cr_n) \cdot S2A + (cr_n)^2 + c\delta_n \cdot (sr_n)^2 \cdot C2A$$

$$m2_n = [(sr_n)^2 + c\delta_n \cdot (cr_n)^2] \cdot S2A + (sr_n \cdot cr_n - c\delta_n \cdot cr_n \cdot sr_n) \cdot C2A$$

$$m3_n = (S2A \cdot cr - C2A \cdot sr) \cdot s\delta$$

where $cr = \cos(2r)$, $sr = \sin(2r)$, $c\delta = \cos(\delta)$, $s\delta = \sin(\delta)$, $C2A = \cos(2A)$, $S2A = \sin(2A)$, $r$ is the retarder azimuthal orientation angle, $\delta$ is the retardance, and $A$ is the analyzer orientation (for most retarders, the retardance varies inversely with wavelength, that is $\delta(\lambda) = \delta_c/\lambda$)

These polarization state modifying vectors can be packed into a (4×4) square transfer matrix "A", such that the measured intensity for each discrete state is given by:

$$I_n = A \cdot I_{S,P} = \begin{pmatrix} I_0 \\ I_1 \\ I_2 \\ I_3 \end{pmatrix} = \begin{pmatrix} m0_0 & m1_0 & m2_0 & m3_0 \\ m0_1 & m1_1 & m2_1 & m3_1 \\ m0_2 & m1_2 & m2_2 & m3_2 \\ m0_3 & m1_3 & m2_3 & m3_3 \end{pmatrix} \cdot \begin{pmatrix} s0 \\ s1 \\ s2 \\ s3 \end{pmatrix}$$

To determine the Stokes Vector incident on the Polarimeter, the transfer matrix "A" s inverted and multiplied times the measured intensities coresponding to each discrete polarization state:

$$\begin{pmatrix} s0 \\ s1 \\ s2 \\ s3 \end{pmatrix} = \begin{pmatrix} m0_0 & m1_0 & m2_0 & m3_0 \\ m0_1 & m1_1 & m2_1 & m3_1 \\ m0_2 & m1_2 & m2_2 & m3_2 \\ m0_3 & m1_3 & m2_3 & m3_3 \end{pmatrix}^{-1} \cdot \begin{pmatrix} I_0 \\ I_1 \\ I_2 \\ I_3 \end{pmatrix}$$

and the sample system parameters:

$$N = \cos(2 \cdot P) - s1$$

$$C = \frac{s2}{\sin(2 \cdot P)}$$

$$S = \frac{-s3}{\sin(2 \cdot P)}$$

can then be extracted. To illustrate this approach, a transfer matrix is constructed assuming nominal azimuthal orientations of (0.0), (90) (+22.5) and (−22.5) degrees for each of the four (4) discrete polarization states. The same nominal retardance is assumed for each retarder. The analytical inversion of this matrix is very complicated, but it is still trivial to numerically invert the matrix given the sample expressions for each element given by:

$$A = \begin{pmatrix} 1 & C2A & c\delta \cdot S2A & S2A \cdot s\delta \\ 1 & C2A & c\delta \cdot S2A & -(S2A \cdot s\delta) \\ 1 & (1-c\delta) \cdot \frac{S2A}{2} + (1+c\delta) \cdot \frac{C2A}{2} & (1+c\delta) \cdot \frac{S2A}{2} + (1-c\delta) \cdot \frac{C2A}{2} & (S2A - C2A) \cdot s\delta \cdot \frac{\sqrt{2}}{2} \\ 1 & -(1-c\delta) \cdot \frac{S2A}{2} + (1+c\delta) \cdot \frac{C2A}{2} & (1+c\delta) \cdot \frac{S2A}{2} - (1-c\delta) \cdot \frac{C2A}{2} & (S2A + C2A) \cdot s\delta \cdot \frac{\sqrt{2}}{2} \end{pmatrix}$$

Multiplying the inverted matrix by the measured intensities for each discrete polarization state allows straight forward determination of the sample system characterizing N, C, S, Ψ, and Δ.

A General Regression Based Approach to Calibration of (DSP-SE$_{tm}$) systems and allow extraction of accurate ellipsometric sample system characterizing data assumes that the (DSP-SE$_{tm}$) system measures polychromatic electromagnetic radiation beam intensity at "n" discrete polarization states, and that "m" samples with different ellipsometric properties are utilized. For a traditional polarimeter system, which is calibrated on a wavelength by wavelength basis, it is necessary to have "m" be greater than or equal to "n". However, utilizing global regression which allows calibration parameters to be parameterized vs. wavelength, (thereby reducing the number of parameters required to describe the system transfer Matrices "A" at each wavelength), it is possible to reduce the number of calibration sample systems required, "m", to be less than "n". Under this approach, calibration of a present invention (DSP-SE$_{tm}$) system, a multi-dimensional data set "I" is measured consisting of measured polychromatic electromagnetic radiation beam intensities for each discrete polarization state, on each calibration sample system, and at each wavelength in the spectral range of the instrument:

$$Igen(p_y)_{i,j,k} = A \cdot \begin{pmatrix} 1 & -N_{j,k} & 0 & 0 \\ -N_{j,k} & 1 & 0 & 0 \\ 0 & 0 & C_{j,k} & S_{j,k} \\ 0 & 0 & -S_{j,k} & C_{j,k} \end{pmatrix} \cdot \begin{pmatrix} s0 \\ s1 \\ s2 \\ s3 \end{pmatrix}$$

To generate "predicted" intensities measured by the (DSP-SE$_{tm}$), (as a function of calibration parameters spsecified in the vector $p_y$), the following equation is applied:

Iexp$_{i,j,k}$ where
i=1 . . . n (for each discrete polarization state)
j=1 . . . m (for each calibration sample)
k=1 . . . w (for each wavelength)

where "A" is an ("n"×4) matrix, in which each row is possibly parameterized by foregoing equation DSP#2 and the input vector s$_n$ is possibly parameterized by the input polarizer azimuth by an equation DSP#1. The extraction of calibration sample system's N, C and S parametres can be calculated as a function of film thickness and angle of incidence (given calibration sample systems which are well characterized by known optical models and optical constants, such as SiO$_2$ on Si films with systematically increasing SiO$_2$ film thicknesses).

To perform regression analysis, the "chi-squared" function:

$$\chi^2 = \sum_{i=1}^{n} \sum_{j=1}^{m} \sum_{k=1}^{w} \left[ \frac{Iexp_{i,j,k}}{\sqrt{\sum_{i=1}^{m} (Iexp_{i,j,k})^2}} - \frac{Igen(p_y)_{i,j,k}}{\sqrt{\sum_{i=1}^{m} (Iexp(p_y)_{i,j,k})^2}} \right]^2$$

is then minimized, (typically utilizing a non-linear regression algorithm such as "Marquard-Levenberg"), by adjusting calibration parameters specified in the vector "$p_y$". To aid in the regression, both the experimental and generated intensity vectors are normalized by the sum of the squares of all the discrete polarization states at each wavelength.

If the global parameterization of calibration parameters is not used, then the vector "$p_y$" consists of the input Stokes Vector values "$s_n$", and the elements of the transfer matrix "A", all of which must be defined at each wavelength, This requires at least (4+(4×n))×w) calibration parameters, assuming that the ellipsometric parameters (N, C and S), for each calibration sample system are exactly known.

Further, if global parameterization is used, the input vector "$s_n$" for all wavelengths can be parameterized by the input polarizer azimuth "p" the ellipsometric parameters of the "m" calibration samples can be parametrically calculated as function of angle of incidence ($\phi_m$) and film thickness "$t_m$" and the transfer matrix "A" can be parameterized by the Azimuth of the analyzer "A", the orientation of each retarder "$r_n$", and the retardance of each retarder as a function of wavelength $S(\lambda)_n \pm \delta c_n/\lambda$. It is noted that higher order terms could also be added to the retardance vs. wavelength function, or to any other of the calibration parameters to improve fit between the experimentally measured and modeled generated data. Such a global parameterization significantly reduces the number of calibration parameters required to describe the (DSP-SE$_{tm}$) system over a spectroscopic range of wavelengths. The total number of calibration parameters in this suggested parameterization (other variations are certainly possible as well), may be as few as:

$p_y = P + \phi_m + t_m + A + r_n + \delta c_m = 1 + m + m + 1 + n + m = (2 \times m) + (2 \times n) + 2$.

To extract the ellipsometric parameters of an arbitrary sample system which is inserted into a general (DSP-SE$_{tm}$) system, a regression analysis can also be performed, and N, C and S can be defined and evaluated by regression at each wavelength separately.

Further, if the plane of incidence of the sample system is allowed to vary slightly, (to account for imperfect alignment to the ellipsometer system), the Stokes Vector which enters the discrete polarization state modifier becomes:

$$M_s \cdot I_p = k \cdot \begin{pmatrix} 1 & 0 & 0 & 0 \\ 0 & \cos(s) & -\sin(s) & 0 \\ 0 & \sin(s) & \cos(s) & 0 \\ 0 & 0 & 0 & 1 \end{pmatrix} \cdot \begin{pmatrix} 1 & -N & 0 & 0 \\ -N & 1 & 0 & 0 \\ 0 & 0 & C & S \\ 0 & 0 & -S & C \end{pmatrix} \cdot$$

$$\begin{pmatrix} 1 & 0 & 0 & 0 \\ 0 & \cos(s) & \sin(s) & 0 \\ 0 & -\sin(s) & \cos(s) & 0 \\ 0 & 0 & 0 & 1 \end{pmatrix} \cdot \begin{pmatrix} 1 \\ 0 \\ 1 \\ 0 \end{pmatrix} = k \cdot \begin{bmatrix} 1 - s \cdot N \\ -N + s \cdot (1-C) \\ -s \cdot N + C \\ -S \end{bmatrix}$$

where "s" is the azimuthal misalignment of the sample system, and presumably is very near zero.

In this case the (DSP-SE$_{tm}$) system, would not measure the "true" N, C and S parameters, but would instead measure "effective" parameters Neff, Ceff and Seff:

Neff=$N-s \cdot (1-C)$

Ceff=$C-s \cdot N$

Seff=$S$

It would be possible to include the azimuthal misalignment factor "s" as a fitting parameter in subsequent analysis of the ellipsometric data measured by a (DSP-SE$_{tm}$) system.

It is believed that the present invention spectroscopic ellipsometer system combination comprising:

Polarizer and analyzer, (which are both fixed in position during data acquisition); and at least one stepwise rotatable compensator means for discretely, sequentially, modifying a polarization state of a beam of electromagnetic radiation provided by said source of polychromatic electromagnetic radiation through a plurality of polarization states, said means being present at at least one location selected from the group consisting of:

between said polarizer and said stage for supporting a sample system; and between said stage for supporting a sample system and said analyzer;

said at least one stepwise rotatable compensator means for discretely, sequentially, modifying a polarization state of a beam of electromagnetic radiation provided by said source of polychromatic electromagnetic radiation through a plurality of polarization states, being positioned so that said beam of electromagnetic radiation transmits therethrough in use;

is Patentably distinct over all prior art other than Patents which are co-owned by the J.A. Woollam Co. Inc.

Patentability is thought to be further enhanced when said present invention spectroscopic ellipsometer system is combined with a reflectometer system, (particularly when said present invention spectroscopic ellipsometer system and reflectometers system share a common source of electromagnetic radiation and/or a multi-element spectroscopic detector thereof), and/or where the source of polychromatic radiation comprises a system for providing an output beam of polychromatic electromagnetic radiation, which has a relatively broad and flattened intensity vs. wavelength characteristic over a wavelength spectrum, which comprises at least a first and a second source of polychromatic electromagnetic radiation; and at least a first electromagnetic beam combining means comprising a plate, (eg. uncoated fused silica or glass etc. such that reflection/transmission characteristics thereof are determined by angle-of-incidence and polarization state of a beam of electromagnetic radiation).

The present invention will be better understood by reference to the Detailed Description Section of this Specification, in combination with the Drawings.

SUMMARY

It is therefore a primary purpose and/or objective of the present invention to disclose spectroscopic ellipsometer and combined spectroscopic reflectometer/ellipsometer systems, as well as methods of calibration therefore; which present invention system includes, in the spectroscopic ellipsometer portion thereof, provision of polarizer and analyzer elements which are fixed in position during data acquisition procedures, and at least one stepwise rotatable compensator means for imposing a plurality of sequentially discrete, rather than continuously varying, polarization states onto a beam of electromagnetic radiation caused to be present in said spectroscopic ellipsometer system.

It is another purpose and/or objective yet of the present invention to disclose a preferred, but not limiting, source of electromagnetic radiation which provides a plurality of wavelengths combined from a plurality of sources.

It is another purpose and/or objective of the present invention to disclose a method of calibration of the spectroscopic ellipsometer system portion of the present invention system which utilizes data obtained utilizing a sequential plurality of polarization states.

Other purposes and/or objectives will become clear from a reading of the Specification and Claims.

BRIEF DESCRIPTION OF THE DRAWINGS

FIGS. 3j1–3p show additional functional construction of compensator systems which are within the scope of the present invention.

FIG. 4 demonstrates the flow of a present invention method of calibration of the spectroscopic ellipsometer portion of the present invention.

DETAILED DESCRIPTION

Figure 14:
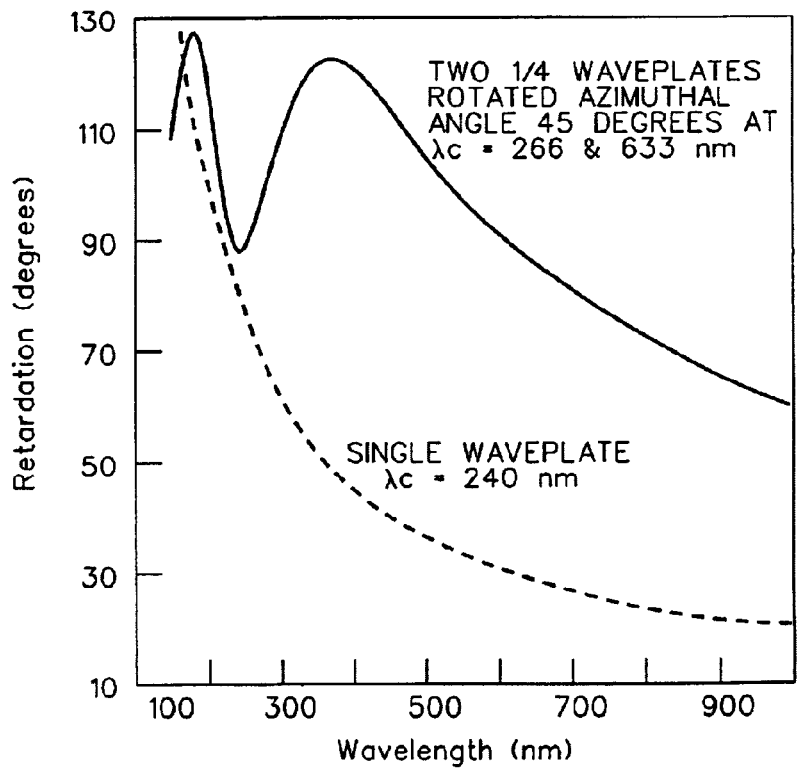
FIGS. 14–16 provide insight to the Psuedo-Achromatic characteristics achieved by a FIG. 3f Compensator design.
Figure 15:
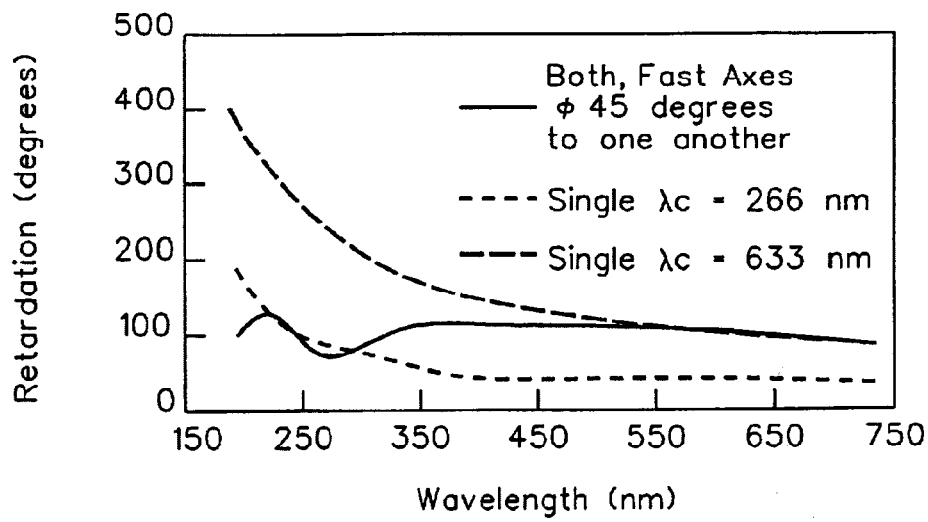
Figure 16:
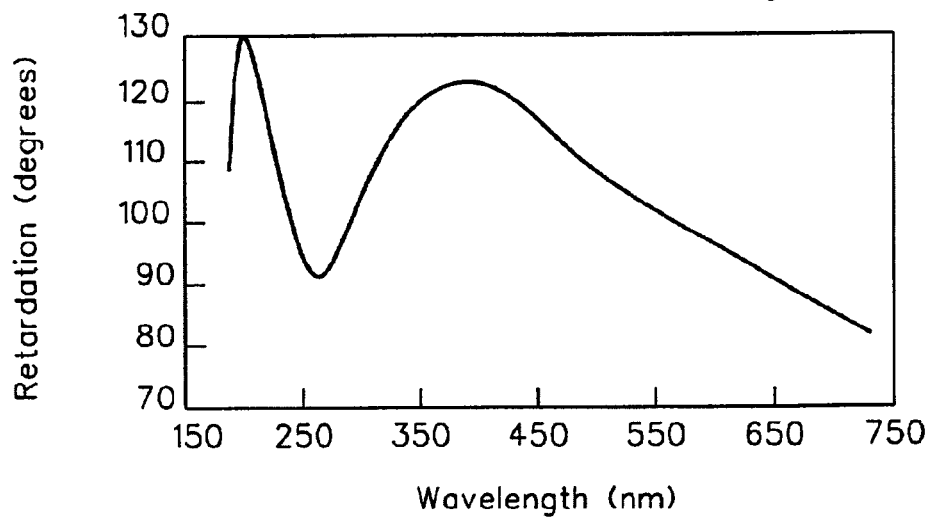

FIGS. 1–3d and 4–13 show material previously disclosed in Co-Pending application Ser. No. 09/517,125, and discussion thereof is repeated herein to provide full disclosure and background for introducing material which is new herewithin. FIGS. 3e–3P demonstrate Compensators for application in the present invention, and FIGS. 14–16 show Retardation vs. Wavelength for Compensator designs which are Pseudo-Achromatic.

Figure 1:
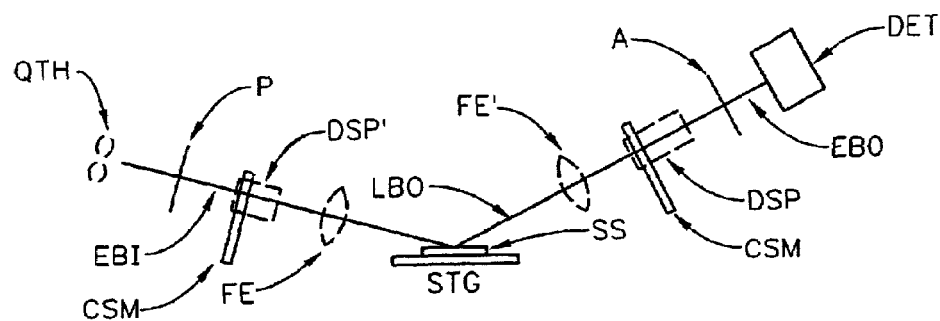
FIG. 1 shows a present invention spectroscopic ellipsometer system configuration.

Turning now to FIG. 1, there is shown a spectroscopic ellipsometer system configuration. Shown are a source of polychromatic electromagnetic radiation (QTH), (eg. a quartz-halogen-lamp), a polarizer (P) a stage for supporting a sample system (STG) with a sample system (SS) present thereupon, a means (DSP) for discretely, sequentially, modifying a polarization state of a beam of electromagnetic radiation provided by said source of polychromatic electromagnetic radiation through a plurality of polarization states by passage therethrough, an analyzer (A), and a detector system (DET). (Note preferred detector systems are spectroscopic multi-element such as Bucket Brigade, Diode and CCD arrays and that "off-the-shelf" spectrometer systems such as manufactured by Zeiss can also be applied). Shown also are ellipsometer electromagnetic beam in (EBI) and ellipsometer electromagnetic beam out (EBO). It is noted that said means (DSP) for discretely, sequentially, modifying a polarization state of a beam of electromagnetic radiation, while shown as present between said stage (STG) for supporting a sample system (SS) and said analyzer (A), can generally be present as (DSP') between said polarizer (P) and said stage (STG) for supporting a sample system (SS), and/or as (DSP) between said stage (STG) for supporting a sample system and said analyzer (A).

Figure 2:
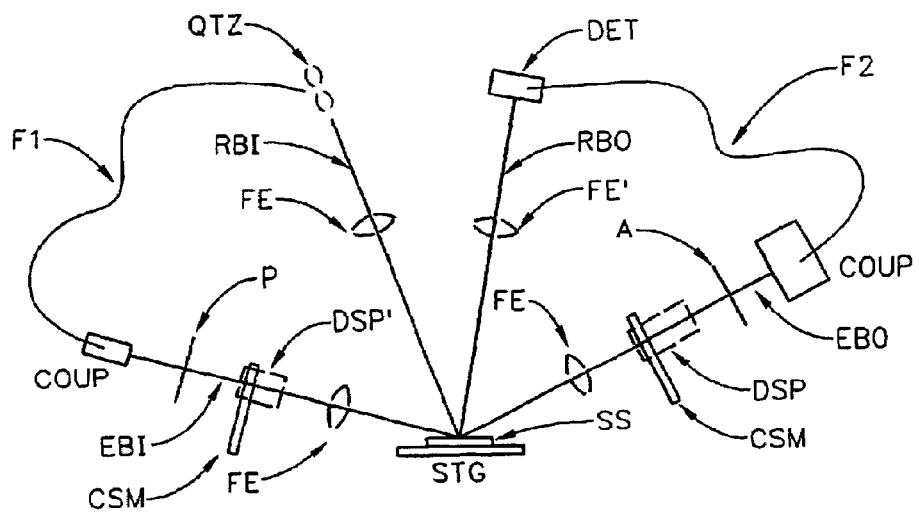
FIG. 2 shows a combined present invention spectroscopic reflectometer/ellipsometer system.

FIG. 2 shows a combined spectroscopic reflectometer/ellipsometer system wherein the source of polychromatic electromagnetic radiation (QTH), and detector (DET) system are common to both, and wherein the spectroscopic ellipsometer system is shown as being provided input and output electromagnetic beam access via fiber optics (F1) and (F2). Shown are near-normal orientation reflectometer electromagnetic beam in (RBI) and reflectometer electromagnetic beam out (RBO), as well as sample system (SS) specific near Brewster condition ellipsometer electromagnetic beam in (EBI) and ellipsometer electromagnetic beam out (EBO). While not shown, it is noted that the source of polychromatic electromagnetic radiation (QTH), and detector (DET) system can be located distal from both the reflectometer and ellipsometer portions of the combined spectroscopic reflectometer/ellipsometer system, with fiber optics being present to interface to the reflectometer portion as well.

In both FIGS. 1 and 2, there can optionally be other (eg. focusing elements ((FE) (FE')), present on one or both sides of the sample system (SS), as shown in dashed lines. Said other elements appear ellipsometrically indistinguishable with polarization state modifiers during use. Also shown in FIGS. 1 & 2 are Compensator Stepping Means (CSM) (CSM') for use in stepwise rotating compensator (DSP) and/or (DSP') or operating means as shown in FIGS. 3a–3c.

Figure 3A:
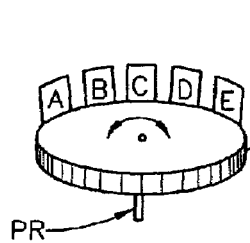
FIG. 3a shows a frontal perspective view of a discrete state polarizer comprising a wheel with five discrete polarizer elements mounted thereupon.

FIG. 3a shows a frontal perspective view of a discrete state polarizer (DSP) comprising an essentially circular "wheel" element (WE) with five discrete polarization state modifiers elements (A) (B) (C) (D) and (E) mounted thereupon on the perimeter thereof, such that said and projecting discrete polarization state modifier elements (A) (B) (C) (D) and (E) project perpendicularly to a surface thereof.

Figure 3B:
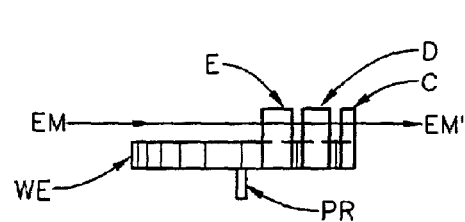
FIG. 3b shows a side elevational view of a discrete state polarizer, as in FIG. 3a, oriented so that an electromagnetic beam passing through one of the discrete polarizer five elements.

FIG. 3b shows a side elevational view of a discrete state polarizer, as in FIG. 3a, oriented so that an electromagnetic beam (EM) passing through one (C) of the five discrete polarization state modifiers (A) (B) (C) (D) and (E) elements. Note that discrete polarizer elements (A) and (B) are located behind discrete polarizer elements (E) and (D) respectively. Also note that if the essentially circular "wheel" element (WE) is caused to rotate about the pivot rod (PR) which projects from a lower surface of said essentially circular "wheel" element, each of the various five discrete polarizer (A) (B) (C) (D) and (E) elements can be rotated into the position in which is shown discrete polarizer element (C).

Figure 3C:
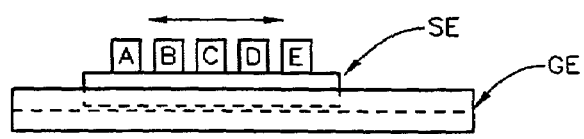
FIG. 3c shows a front elevational view of a discrete state polarizer with five laterally slideably mounted discrete polarizer elements mounted therein.

FIG. 3c shows a front elevational view of a discrete state polarizer with five laterally slideably mounted discrete polarizer (A) (B) (C) (D) and (E) elements mounted on a slider element (SE) which is mounted in a guide providing element (GE) therein. Sliding the slider element (SE) to the right or left serves to position each of the five discrete polarizer (A) (B) (C) (D) and (E) elements in a position at which an electromagnetic beam of radiation can be caused to be present. (Note more or less than five discrete polarizer elements can be present).

Figure 3D:
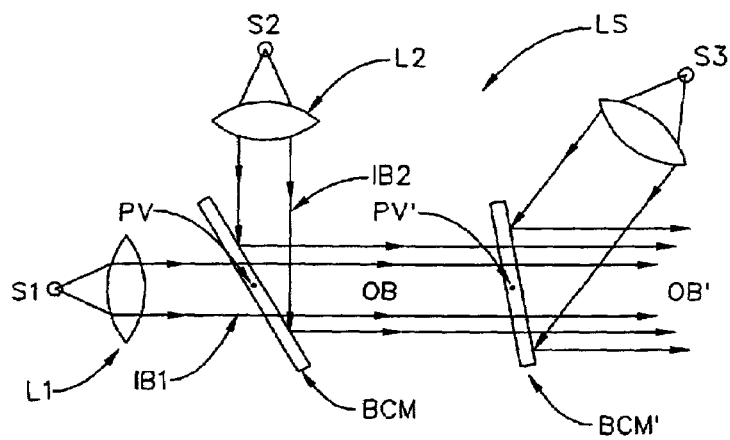
FIG. 3d shows a present invention system for providing an output beam (OB) or (OB') of polychromatic electromagnetic radiation which has a relatively broad and flattened intensity vs. wavelength characteristic over a wavelength spectrum.

The embodiments in FIGS. 3a–3c have been found to be difficult to practice, however, and it has been determined that a beter appraoch is to utilize rotatable compensator means to provide the discrete polarization state changes. FIGS. 3e, 3f, 3g, 3h and 3i demonstrate that at least one Compensator can be applied as (DSP) or (DSP') in FIGS. 1 and 2, which at least one Compensator (DSP) and/or (DSP'), is, in use, rotated about the locus of the electromagnetic beam (EBI) or (EBO), by Compensator Rotation Stepping Means (CSM') and/or (CSM). That is, the presently disclosed invention then comprises a Discrete Polarization State Spectroscopic Ellipsometer System, with the clarification being that the Discrete Polarization State effecting means (DSP) and/or (DSP') is preferably a Rotatable Compensator, which during use is stepped through a plurality of discrete rotation angles, and then held motionless during data acquisition. While not limiting, a utility providing specific embodiment applies Psuedo-Achromatic Rotatable Compensators. (Note, FIGS. 14–16 show various Psuedo-Achromatic Retardation vs. Wavelength characteristics possible utilizing multiple element compensators, as shown in FIG. 3f).

Further, essentially any Compensator which can be placed into a beam of electromagnetic radiation can be applied, such as those disclosed in claim 9 of U.S. Pat. No. 5,872,630, (which 630 Patent is incorporated by reference hereinto):

Berek-type;
Non-Berek-type;
Zero Order;
Zero Order comprising a plurality of plates;
Rhomb;
Polymer;
Achromatic Crystal; and
Psuedo-Achromatic.

Figure 3E:
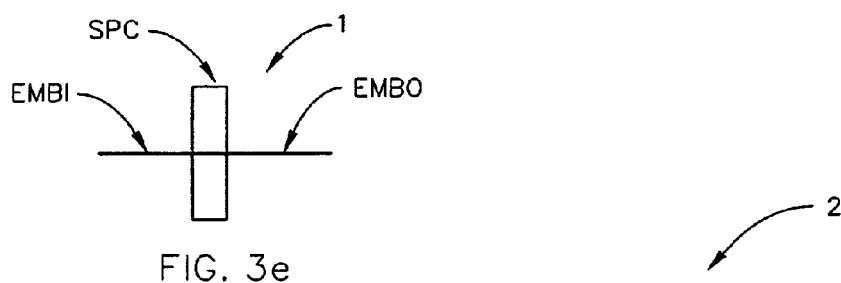
FIGS. 3e–3i demonstrate functional construction of preferred present invention compensator systems.
Figure 3F:
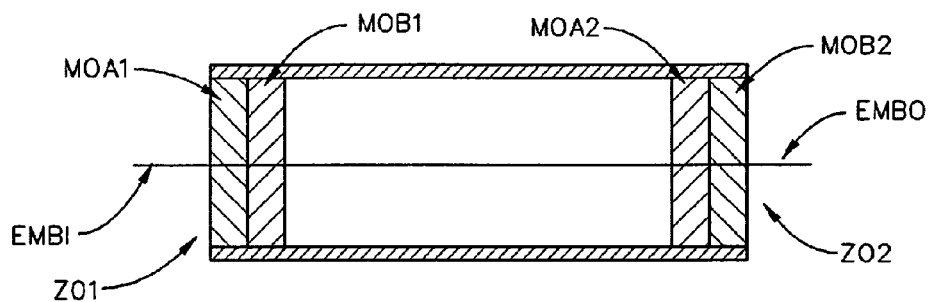
Figures 3G, 3H:
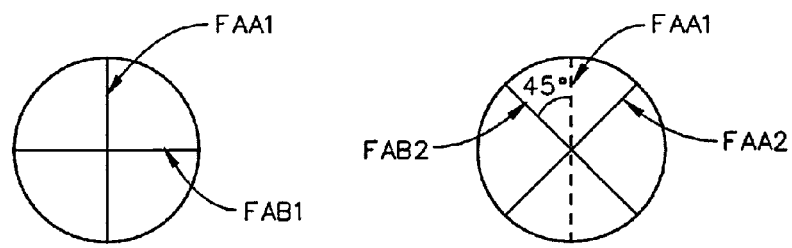
Figure 3I:
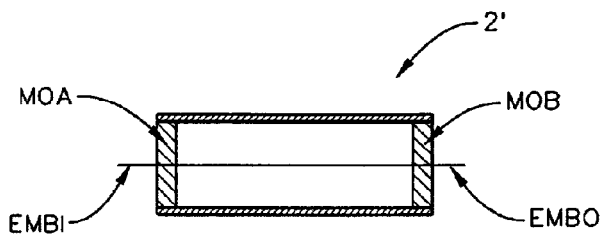

FIGS. 3e, 3f, 3g, 3h and 3i demonstrate functional construction of preferred present invention compensator systems. FIG. 3e simply exemplifies that a single plate (SPC) compensator (1) can be applied. FIG. 3f demonstrates construction of a compensator (2) from first (ZO1) and second (ZO2) effectively Zero-Order, (eg. Quartz or Bicrystaline Cadmium Sulfide or Bicrystaline Cadmium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 14b is a cross-sectional side view of a present invention preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof with a Retardation vs. Wavelength. FIGS. 3g and 3h are views looking into the left and right ends of the preferred present invention Compensator (PC) as shown in FIG. 3f, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB2) of the first effective Zero-Order Waveplate (ZO1). (Note that the fast axis (FAA1) of the first effective Zero-Order Waveplate (ZO1) is shown as a dashed line in FIG. 3h, for reference). FIG. 3i demonstrates functional construction of another preferred compensator (2') which is constructed from two per se. single plate Zero-Order Waveplates (MOA) and (MOB), which are typically made of materials such as mica or polymer.

(It is specifically to be understood that a present invention compensator system can be comprised of at least one Zero-Order waveplate and at least one effectively Zero-Order waveplate in combination, as well as combinations comprised of two actual Zero-Order waveplates or two effectively Zero-Order waveplates).

FIGS. 3j1–3p demonstrate additional compensators which can be applied in the present invention.

FIG. 3j1 shows that the first additional present invention retarder system (3) comprises a first triangular shaped element (P1), which as viewed in side elevation presents with first (OS1) and second (OS2) sides which project to the left and right and downward from an upper point (UP1). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of material which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 3j1, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughput. Also, assuming accurately manufactured right angle first (P1) and second (P2) triangular shaped elements are utilized, this compensator design provides inherent compensation of both angular and translational misalignments of the input light beam (LB). As well, the total retardence provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (3) is present will require calibration to characterize the PSI-like component thereof.

FIG. 3j2 shows a variation (3') on FIG. 3j1, wherein the first triangular shaped element is replaced by two rotatable reflecting means, identified as (OS1') and (OS2'). This modification allows user adjustment so that the locus of an entering electromagentic beam (LB') exits undeviated and undisplaced from an entering electromagentic beam (LB).

FIG. 3k shows that the second additional present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos(α)), where alpha (α) is shown as an angle at which said right (RS) and left (LS) sides project from horizontal. Said retarder system (4) is made of a material with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam or radiation at said internal reflections from the top (TS) and bottom (BS) surfaces. This retarder system is very robust as it is made of single piece construction. It is noted that adjustment of the angle alpha (α) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula which defines the retardation provided thereby being:

$$\frac{d}{h} = 2 - \tan(\phi), \text{ where } \phi = \alpha \cdot \sin^{-1}\left(\frac{\sin(90 - \alpha)}{n}\right)$$

Figure 3L:
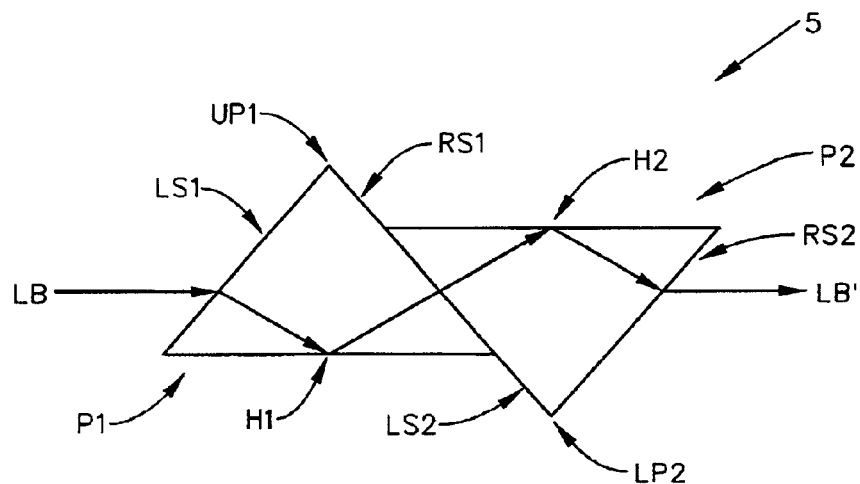

FIG. 3l shows that the third additional present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) sides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of material with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that The triangular shape elements (P1) and/or (P2) can be made of various materials with various indicies of refraction, and coating(s) can be applied to one or both of the third sides (H1) and (H2) of said first (P1) and second (P2) triangular shaped elements to adjust retardation entered to an electromagnetic beam (LB1).

Figure 3M:
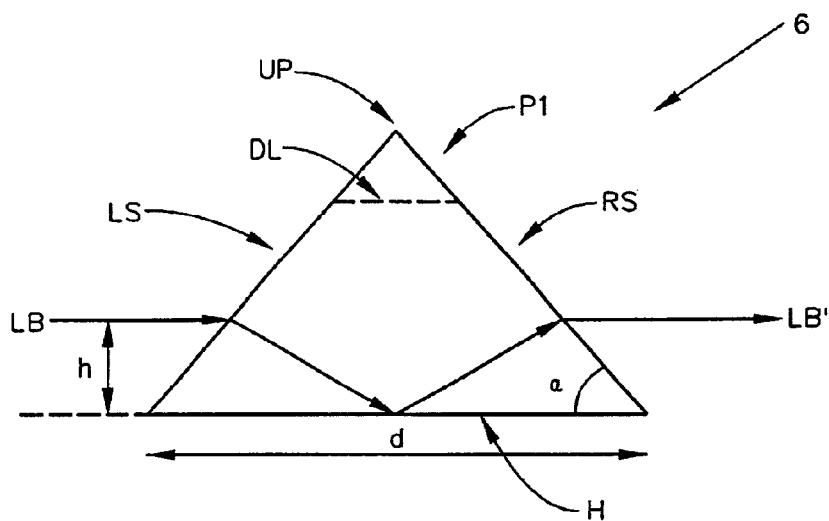
Figure 5:
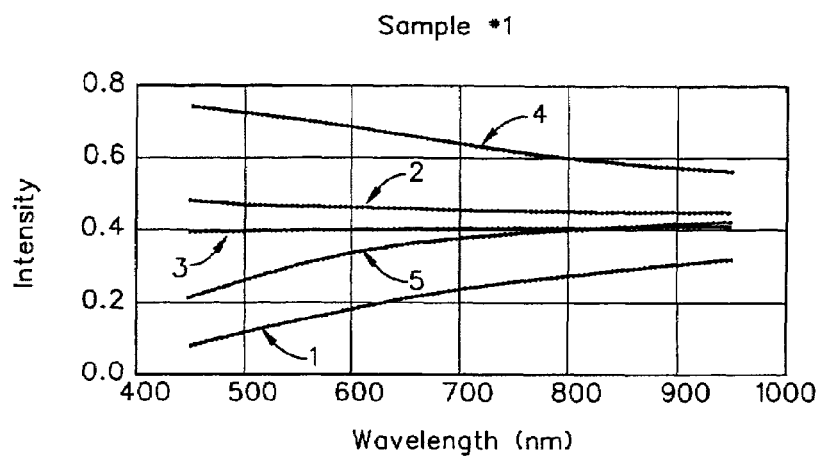
FIGS. 5–11 show Intensity vs. Wavelength for the seven (7) ellipsometrically different samples, obtained by fitting a mathematical model of the samples and the spectroscopic ellipsometer system by regression onto experimentally obtained data obtained at each of five (5) discrete polarization states.
Figure 6:
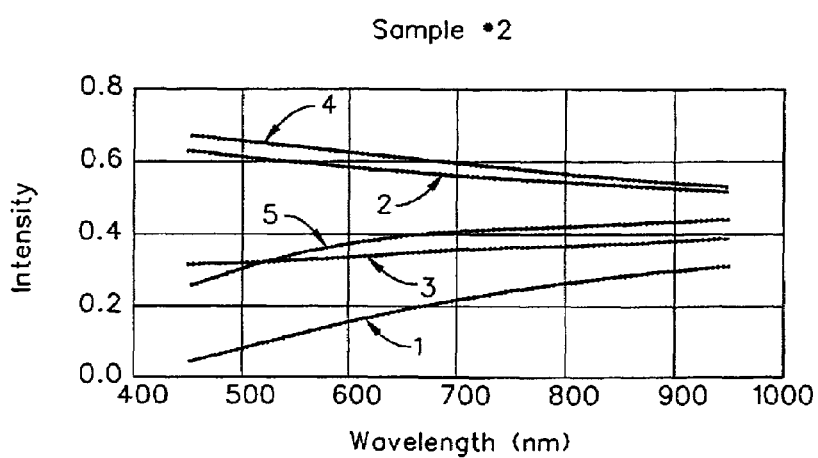
Figure 7:
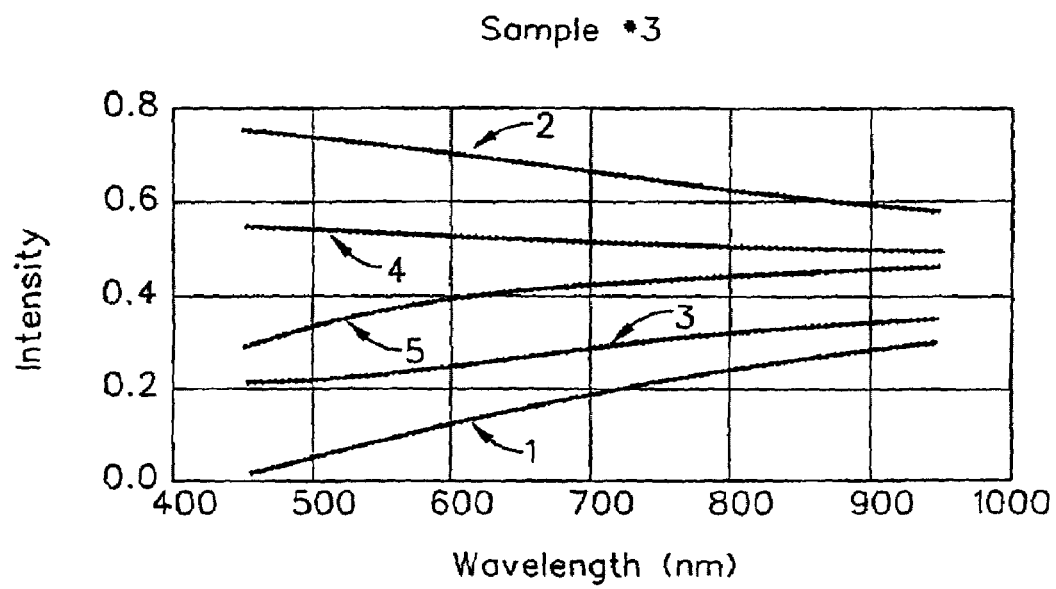
Figure 8:
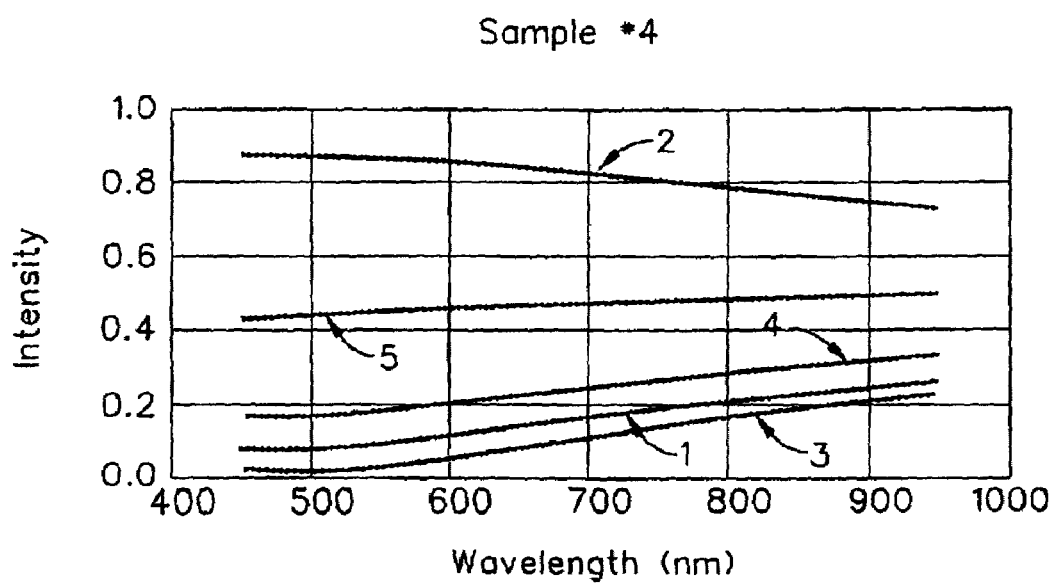
Figure 9:
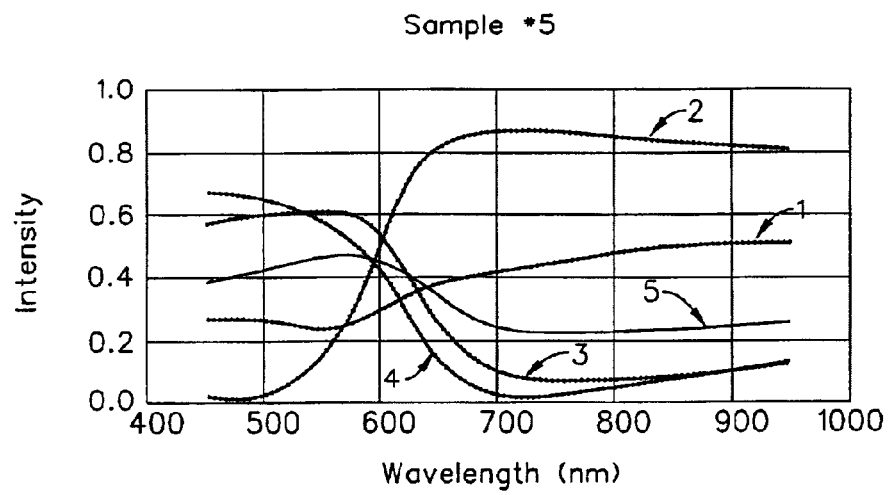
Figure 10:
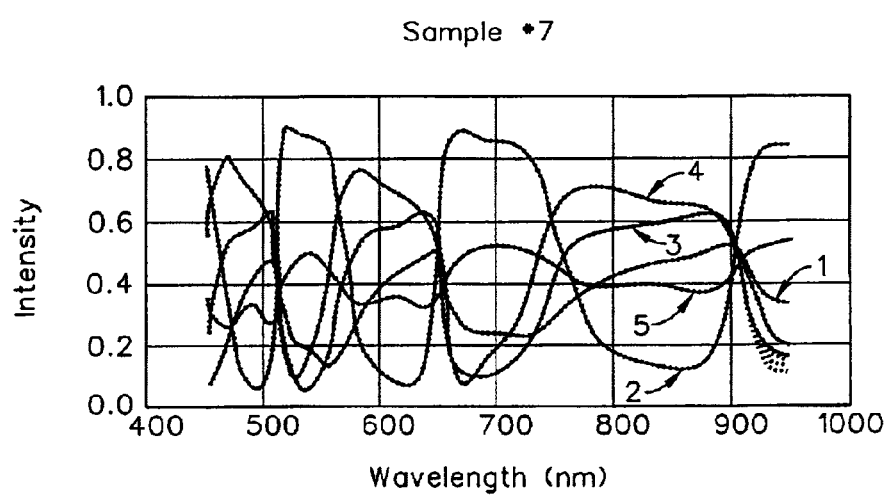
Figure 11:
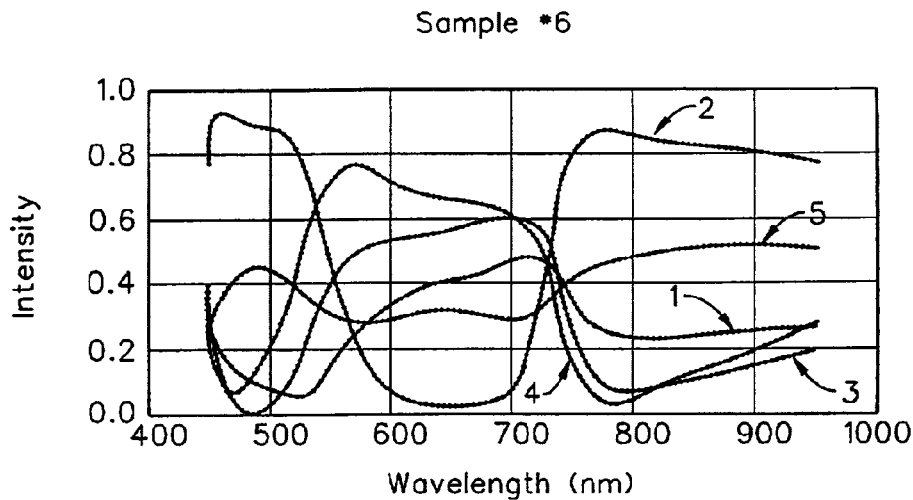

FIG. 3m shows that the forth additional present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS) and second (RS) sides. Said retarder system (6) is made of a material with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 3m retarder system (6) is typically an isosceles prism which is available off-the-shelf with an angle alpha (α) of forty-five (45) degrees. As long as the input electromagnetic beam (LB) height (h) is chosen in accordance with the formula:

$$d = 2h\left(\frac{1}{\tan(\alpha)} + \tan(\phi)\right), \text{ where } \phi = \alpha + \sin^{-1}\left(\frac{\sin(90 - \alpha)}{n}\right)$$

in conjunction with the index of refraction (n) of the material from which the retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics.

FIG. 3*p* shows that the fifth additional present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2) and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of material with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side LS1) of said first parallelogram shaped element (PA1) along an essentially horizontally oriented locus, is caused to diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB).

This is the case even when said retarder system (7) is caused to rotate. The result of said described retarder system (7) application being that retardation is entered between orthogonal components of said input electromagnetic beam of radiation (LB).

FIG. 3*n*1 shows that the sixth additional present invention retarder system (8) comprises first (BK1) and second (BK2) Berek-type retarders which each have an optical axes essentially perpendicular to a surface thereof. As shown by FIG. 3*n*2, each of said first (BK1) and second (BK2) Berek-type retarders can have fast axis which are oriented other than parallel to one another, but for the presently described retarder system it is assumed that the fast axes are aligned, (ie. an angle PHI (ϕ) of zero (0.0) degrees exists between fast axes of the two Berek-type (BK1) and (BK2) plates in FIG. 3*n*1. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardence introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately hal of achieved retardance. This insensitivity results because if the input electromagnetic beam is slightly changed, one of said plates will contribute slightly more (less), but the second slightly less (more) retardence because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardence characteristic which, without more, makes use over a wide spectral range difficult.

A variation of the just described retarder system (8) applies to the seventh additional present invention retarder system (9) as well, with the difference being that a FIG. 3*n*2 offset angle PHI (ϕ) other than zero (0.0) is present between fast axes of the two Berek-type plates. The description of the system remains otherwise unchanged. The benefit derived, however, is that a flatter than (1/wavelength) retardation characteristic can be achieved thereby.

FIG. 3*o*1 serves as the pictorial reference for the eighth additional present invention retarder system (10) which comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. This is exemplified by FIG. 3*o*2. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB") passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

A ninth additional present invention retarder system (11) is also pictorially represented by FIG. 3o1 and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/ ((BK1) and (BK2)). This embodiment includes the case where all the fast axes of all Berek-type retarders (BK1), (BK2), (BK3) and (BK4) are all different.

Turning now to FIG. 3d, it is shown that the present invention system source of polychromatic radiation (QTH) as in FIG. 1, can, but not necessarily, be a system for providing an output beam (OB) of polychromatic electromagnetic radiation which has a relatively broad and flattened intensity vs. wavelength characteristic over a wavelength spectrum (generally identified as (LS)), said output beam (OB) of polychromatic electromagnetic radiation substantially being a comingled composite of a plurality of input beams, ((IB1) and (IB2)), of polychromatic electromagnetic radiation which individually do not provide as relatively broad and flattened a intensity vs. wavelength characteristic over said wavelength spectrum, as does said output comingled composite beam of polychromatic electromagnetic radiation, said system for providing an output beam of polychromatic electromagnetic radiation which has a relatively broad and flattened intensity vs. wavelength characteristic over a wavelength spectrum comprising:

a. at least a first (S1) and a second (S2) source of polychromatic electromagnetic radiation, ((IB1) and (IB2) respectively); and b. at least one electromagnetic beam combining (BCM) means comprising an uncoated plate, (eg. uncoated fused silica or glass etc. such that transmission characteristics thereof are determined by angle-of-incidence and polarization state of a beam of electromagnetic radiation).

The at least one electromagnetic beam combining means (BCM) is positioned with respect to said first (S1) and second (S2) sources of polychromatic electromagnetic radiation, ((IB1) and (IB2) respectively), such that a beam of polychromatic electromagnetic radiation (IB1) from said first (S1) source of polychromatic electromagnetic radiation passes through said at least one electromagnetic beam combining means (BCM), and such that a beam of polychromatic electromagnetic radiation (IB2) from said second (S2) source of polychromatic electromagnetic radiation reflects from said at least one electromagnetic beam combining means (BCM) and is comingled with said beam of polychromatic electromagnetic radiation (IB1) from said first source (S1) of polychromatic electromagnetic radiation which passes through said at least one electromagnetic beam combining means (BCM). The resultant beam of polychromatic electromagnetic radiation (OB) is substantially an output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic. Also shown in FIG. 3d are collimating lenses (L1) and (L2) to provide collimated electromagnetic radiation to the electromagnetic beam combining means (BCM), from first (S1) and a second (S2) source of polychromatic electromagnetic radiation, ((IB1) and (IB2) respectively).

FIG. 3d further demonstrates an optional third source of polychromatic electromagnetic radiation (S3) and a second electromagnetic beam combining means (BCM'). The second electromagnetic beam combining means (BCM') is positioned with respect to said comingled beam of polychromatic electromagnetic radiation (OB), (which has a relatively broad and flattened intensity vs. wavelength over a wavelength spectrum, comprising wavelengths from sources (S1) and (S2), which exits said at least a first electromagnetic beam combining means (BCM)), such that said comingled beam of polychromatic electromagnetic radiation (OB) which has a relatively broad and flattened intensity vs. wavelength over a wavelength spectrum, passes through said second electromagnetic beam combining means (BCM). The second electromagnetic beam combining means (BCM) is positioned with respect to said third source of polychromatic electromagnetic radiation (S3) such that a beam of electromagnetic radiation from said third source of polychromatic electromagnetic radiation (S3)

reflects from said second electromagnetic beam combining means (BCM) to form a second resultant beam of polychromatic electromagnetic radiation (OB') which is substantially an output beam of polychromatic electromagnetic radiation which has an even more relatively broadened and flattened intensity vs. wavelength over a wavelength spectrum comprising said comingled composite of a plurality of input beams of polychromatic electromagnetic radiation, (from sources (S1), (S2) and (S3)), which sources (S1), (S2) and (S3) individually do not provide such an even more relatively broadened and flattened intensity vs. wavelength over a wavelength spectrum characteristic. Note that first or second resultant beam of polychromatic electromagnetic radiation (OB) (OB') in FIG. 3d can be comprise the source (QTH) in FIG. 1.

A system as shown in FIG. 3d can also include a pivot(s) (PV) (PV') to allow the beam combining means (BCM) and/or (BCM'), respectively, to be rotated. This can be beneficially applied to allow selection of an optimum angle at which a beam of electromagnetic radiation is caused to reflect therefrom in use. It is noted that the angle at which a beam of electromagnetic radiation approaches a beam combining means affects the percent of an impinging beam which actually reflects therefrom and becomes part of the output beam (OB), and where a beam source positioning can be changed along with pivoting of a beam combining means, this allows optimum combining of transmitted and reflected beams. Also, pivot with two degrees of rotational freedom can be applied to simply effect coincidence of transmitted and reflected beams of electromagnetic radiation which originate from sources which are fixed in location.

Further, as described in the Disclosure of the invention Section of this Specification, as the polarizer in the present invention spectroscopic ellipsometer system remains fixed in position during data acquisition, it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between transmission and reflection "S" polarization components is less, as a function of wavelength and electromagnetic beam angle-of-incidence to said beam combining means, compared to that between the "P" components.

It is noted that any of said sources (S1) (S2) and (S3) of polychromatic electromagnetic radiation can be Xenon or Duterium, and Quartz-Halogen lamps, or other suitable source.

It is also noted that a suitable electromagnetic beam combining (BCM) means can be made of glass or a fused silica plate, (preferably uncoated), and can also be "Hot Mirrors" which reflect IR and transmit visual wavelengths, or "Cold Mirrors" which reflect visible and transmit IR; mirror-type Beamsplitters or Pellicle Beamsplitters, such as described in Edmund Industrial Optics Catalog Number N997A.

It is also generally noted that the present invention spectroscopic ellipsometer system can, but not necessarily, utilize Zeiss Diode Array Spectrometer Systems identified by manufacturer numbers in the group: (MMS1 (300–1150 nm); UV/VIS MMS (190–730 nm); UV MMS (190–400 nm); and IR MMS (900–2400 nm)) as Detector System (DET). Said identified Zeiss systems provide a very compact system comprising a multiplicity of Detector Elements and provide focusing via a Focusing Element, Slit, and single concave holographic grating dispersive optics. However, any functional multi-element spectroscopic Detector arrangement is within the scope of the present invention.

Contuinuing, FIG. 4 demonstrates the flow of a present invention method of calibration of the spectroscopic ellipsometer portion of the present invention.

FIGS. 5–11 show Intensity vs. Wavelength for the seven (7) ellipsometrically different samples at each of five (5) imposed polarization states. Results shown in FIGS. 5–7 respectively, are for Samples identified as 1, 2, 3, 4, 5, 6, and 7, which respectively have Oxide depths atop thereof of, (in Angstroms), 17.50; 103.0; 193.0; 508.0; 1318.0; 4817.0 and 9961.0.

Figure 12:
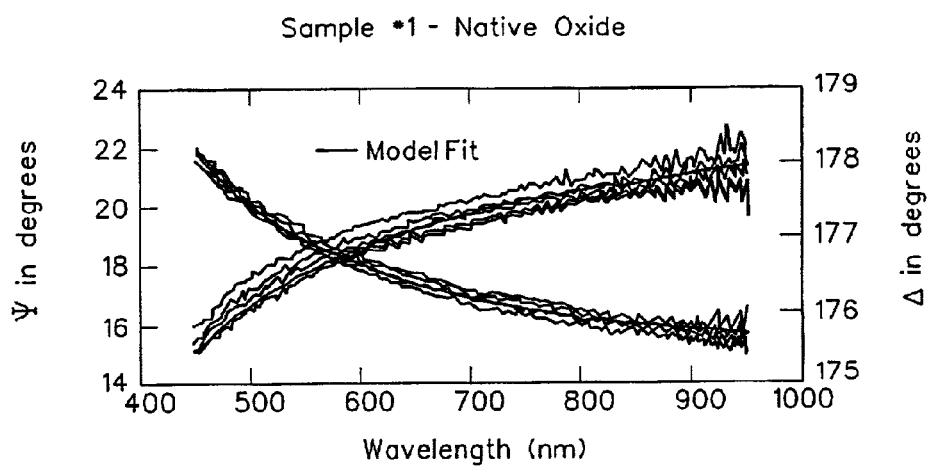
FIGS. 12 & 13 show PSI and DELTA values obtained for samples with thin and thick layers of Oxide thereupon.
Figure 13:
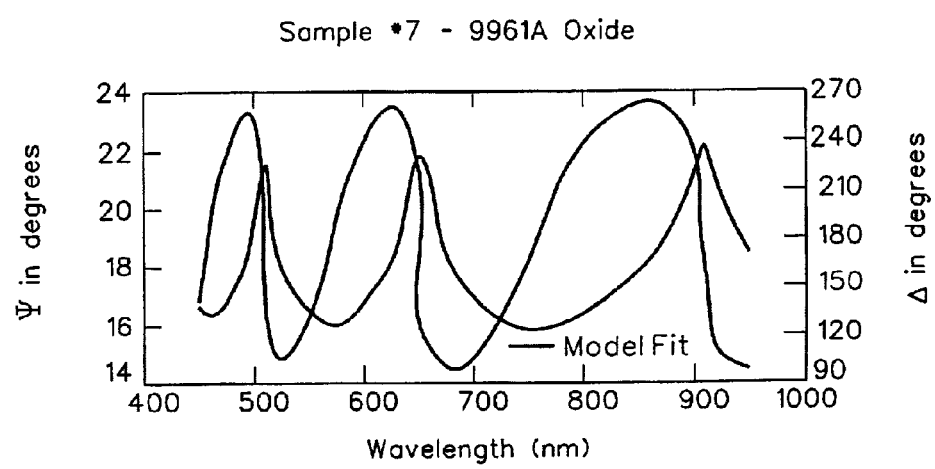

FIGS. 12 & 13 show PSI and DELTA values obtained for samples with thin (native), and thick, (9961 Angstrom), layers of Oxide thereupon. All results were obtained by fitting a mathematical model of the sample system and the spectroscopic ellipsometer system by regression onto experimental data.

FIGS. 14–16 are also included herein to provide insight to the Psuedo-Achromatic characteristics achieved by the FIG. 3f Compensator design. FIG. 14 shows a plot of such a compensator retardation characteristic which depends as (1/wavelength), (dashed line), as well as a present invention compensator charactristic, (solid line). The important thing to note is that a selected range of wavelengths over which a retardation of between seventy-five (75) and one-hundred-thirty (130) degrees is developed, is much greater for the present invention compensator. A present invention spectroscopic rotatable compensator ellipsometer system can comprise at least one compensator(s) which produces a retardance of, preferably, between seventy-five (75) and one-hundred-thirty (130) degrees over a range of wavelengths defined by a selection from the group consisting of:

a. between one-hundred-ninety (190) and seven-hundred-fifty (750) nanometers;

b. between two-hundred-forty-five (245) and nine-hundred (900) nanometers;

c. between three-hundred-eighty (380) and seventeen-hundred (1700) nanometers;

d. within a range of wavelengths defined by a maximum wavelength (MAXW) and a minimum wavelength (MINW) wherein the ratio of (MAXW)/(MINW) is at least one-and-eight-tenths (1.8). Acceptable practice however, provides for the case wherein at least one of said at least one compensator(s) provides a retardation vs. wavelength characteristic retardation between thirty (30.0) and less than one-hundred-thirty-five (135) degrees over a range of wavelengths specified from MINW to MAXW by a selection from the group consisting of:

a. MINW less than/equal to one-hundred-ninety (190) and MAXW greater than/equal to seventeen-hundred (1700);

b. MINW less than/equal to two-hundred-twenty (220) and MAXW greater than/equal to one-thousand (1000) nanometers;

c. within a range of wavelengths defined by a maximum wavelength (MAXW) and a minimum wavelength (MINW) range where (MAXW)/(MINW) is at least four-and one-half (4.5).

(NOTE, the specified vales and ranges can not be achieved by single plates with (1/wavelength) retardation characteristics).

More specifically, FIG. 15 shows calculated retardation vs. wavelength curves for two compensators which demonstrate (1/wavelength) retardation characerics, (long and short dashed lines), and the retardation curve, (solid line), of a present invention assembly configuration as demonstrated in FIG. 3f which is arrived at by combining said two retarders with a 45 degree angle between the fast axes thereof. FIG. 16 shows a re-scaled plot of the solid line curve shown in FIG. 15.

Again, it is emphasised that the present Application does not apply Compensators in a system which causes continuous rotation thereof during data acquisition, but can benefit from a Compensator designed to provide essentially constant Polarization State Modification effects over a Spectroscopic range of wavelengths.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a Polarization state of a beam of electromagnetic radiation Provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;
in which said at least one rotatable compensator comprises at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees.

2. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;
in which said at least one rotatable compensator comprises a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1).

3. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;

in which said at least one rotatable compensator comprises at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1).

4. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;
in which said at least one rotatable compensator comprises at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB)).

5. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of;
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;
in which said at least one rotatable compensator comprises a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation.

6. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation Provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;
in which said at least one rotatable compensator comprises, as viewed in upright side elevation, first and second orientation adjustable mirrored elements which each have reflective surfaces; said compensator system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation; with a result being that retardation is entered between orthogonal components of said input electromagnetic beam of radiation.

7. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation; in which said at least one rotatable compensator comprises a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of:
right and left;
along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of
left and right respectively;
along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation.

8. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:

between said polarizer and said stage for supporting a sample system; and between said stage for supporting a sample system and said analyzer;

and positioned so that said beam of electromagnetic radiation transmits therethrough in use;

in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;

in which said at least one rotatable compensator comprises first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of:

first and second;

not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of:

second and first;

not in contact with said other triangular shape element, along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation.

9. A spectroscopic ellipsometer system comprising:
   a source of polychromatic electromagnetic radiation;
   a polarizer which is fixed in position during data acquisition;
   a stage for supporting a sample system;
   an analyzer which is fixed in position during data acquisition; and
   a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:

between said polarizer and said stage for supporting a sample system; and between said stage for supporting a sample system and said analyzer;

and positioned so that said beam of electromagnetic radiation transmits therethrough in use;

in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;

in which said at least one rotatable compensator comprises a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of:

first and second;

along an essentially horizontally oriented locus, is caused to diffracted inside said retarder system and follow a locus which causes it to essentially totally internally reflect from internal interface of said third sides, and emerge from said retarder from a side selected from the group consisting of second and first respectively;

along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation.

10. A spectroscopic ellipsometer system comprising:
   a source of polychromatic electromagnetic radiation;
   a polarizer which is fixed in position during data acquisition;
   a stage for supporting a sample system;
   an analyzer which is fixed in position during data acquisition; and
   a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:

between said polarizer and said stage for supporting a sample system; and between said stage for supporting a sample system and said analyzer;

and positioned so that said beam of electromagnetic radiation transmits therethrough in use;

in which said at least one means for discretely, sequentially modifying a polarization state of a beam of electromagnetic radiation provided by said source of polychromatic electromagnetic radiation through a plurality of polarization states, involves at least one rotatable compensator that chances the phase angle between orthogonal components of said electromagnetic beam of radiation provided by said source of polychromatic electromagnetic radiation;

in which said at least one rotatable compensator comprises first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of:

parallel to one another; and other than parallel to one another;

said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; with a result being that retardation is entered between orthogonal components of said input electromagnetic beam of radiation.

11. A spectroscopic ellipsometer system comprising:

a source of polychromatic electromagnetic radiation;

a polarizer which is fixed in position during data acquisition;

a stage for supporting a sample system;

an analyzer which is fixed in position during data acquisition; and a multi-element spectroscopic detector system;

said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:

between said polarizer and said stage for supporting a sample system; and between said stage for supporting a sample system and said analyzer;

and positioned so that said beam of electromagnetic radiation transmits therethrough in use;

in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;

in which said at least one rotatable compensator comprises first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type, retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation; with a result being that retardation is entered between orthogonal components of said input electromagnetic beam of radiation.

12. A spectroscopic ellipsometer system comprising:
a source of polychromatic electromagnetic radiation:
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;
in which said at least one rotatable compensator comprises first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation; with a result being that retardation is entered between orthogonal components of said input electromagnetic beam of radiation.

13. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;
in which said source of polychromatic electromagnetic radiation comprises an output beam of polychromatic electromagnetic radiation which has a relatively broad and flattened intensity vs. wavelength characteristic over a wavelength spectrum for use in said present invention systems, provides that said output beam of polychromatic electromagnetic radiation substantially be a comingled composite of a plurality of input beams of polychromatic electromagnetic radiation which individually do not provide as relatively broad and flattened a intensity vs. wavelength characteristic over said wavelength spectrum, as does said output comingled composite beam of polychromatic electromagnetic radiation, said system for providing an output beam of polychromatic electromagnetic radiation which has a relatively broad and flattened intensity vs. wavelength characteristic over a wavelength spectrum comprising:

a. at least a first and a second source of polychromatic electromagnetic radiation; and b. at least a first electromagnetic beam combining means; said at least a first electromagnetic beam combining means being positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

14. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:
between said polarizer and said stage for supporting a sample system; and
between said stage for supporting a sample system and said analyzer;
and positioned so that said beam of electromagnetic radiation transmits therethrough in use;
in which said at least one means for discretely, sequentially, modifying a polarization state of a beam of electromagnetic radiation provided by said source of polychromatic electromagnetic radiation through a plurality of polarization states, involves at least one rotatable compensator that changes the phase angle between orthogonal components of said electromagnetic beam of radiation provided by said source of polychromatic electromagnetic radiation;
in which at least one selection is made from the group consisting of:

at least one of said polarizer and analyzer has its azimuthal angle set to a selection from the group consisting of:
essentially plus forty-five (45) degrees; and
essentially minus forty-five (45) degrees; and
in which said polarizer is set so as to select an "S" polarized electromagnetic beam component referenced to the source of said electromagnetic beam.

15. A method of calibrating a spectroscopic ellipsometer system comprising the steps of:

a. providing a spectroscopic ellipsometer system comprising:
a source of polychromatic electromagnetic radiation;
a polarizer which remains fixed in position during data acquisition;
a stage for supporting a sample system;
an analyzer which remains fixed in position during data acquisition; and
a multi-element spectroscopic detector system;
said spectroscopic ellipsometer system further comprising at least one rotatable compensator means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization states being present at at least one location selected from the group consisting of:
between said polarizer and said stage for supporting a sample system; and
between said stage for supporting a sample system and said analyzer;
and positioned so that said beam of electromagnetic radiation transmits therethrough in use;
said method further comprising, in any functional order, the steps of:

b. for each of at least two ellipsometrically distinguished sample systems, obtaining at least one multi-dimensional data set(s) comprising intensity as a function of wavelength and a function of a plurality of discrete settings of said at least one means for discretely, sequentially, modifying a polarization state of a beam of electromagnetic radiation provided by said source of polychromatic electromagnetic radiation;

c. providing a mathematical model of the ellipsometer system, including provision for accounting for the settings of said at least one means for discretely, sequentially, modifying a polarization state of a beam of electromagnetic radiation provided by said source of polychromatic electromagnetic radiation utilized in step b; and d. by simultaneous mathematical regression onto said data sets, evaluating parameters in said mathematical model, including polarization state changing aspects of each of said plurality of discrete settings of said at least one means for discretely, sequentially, modifying a polarization state of a beam of electromagnetic radiation provided by said source of polychromatic electromagnetic radiation;

in which the step of providing a means for discretely, sequentially, modifying a polarization state of a beam of electromagnetic radiation provided by said source of polychromatic electromagnetic radiation through a plurality of polarization states, involves providing at least one compensator means that changes the phase angle between orthogonal components of said electromagnetic beam of radiation provided by said source of polychromatic electromagnetic radiation;

said at least one compensator means comprising at least one rotatable compensator selected from the group consisting of:

a. a selection from the group consisting of:
  a single element compensator; and
  a multiple element compensator;

b. a compensator comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;

c. a compensator comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

d. a compensator comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

e. a compensator comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

f. a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation;

g. a compensator system comprised of, as viewed in upright side elevation, first and second orientation adjustable mirrored elements which each have reflective surfaces; said compensator system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation; with a result being that retardation is entered between orthogonal components of said input electromagnetic beam of radiation;

h. a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of:

right and left;
along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of:
  left and right respectively;
along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation;
i. a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of:
  first and second;
not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of:
  second and first;
not in contact with said other triangular shape element, along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation;
j. a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of:
  first and second;
along an essentially horizontally oriented locus, is caused to diffracted inside said retarder system and follow a locus which causes it to essentially totally internally reflect from internal interface of said third sides, and emerge from said retarder from a side selected from the group consisting of:
  second and first respectively;
along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation;
k. a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of:
  parallel to one another; and
  other than parallel to one another;
said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; with a result being that retardation is entered between orthogonal components of said input electromagnetic beam of radiation;
l. a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation; with a result being that retardation is entered between orthogonal components of said input electromagnetic beam of radiation;

m. a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation; with a result being that retardation is entered between orthogonal components of said input electromagnetic beam of radiation.

16. A method of calibrating a spectroscopic ellipsometer system as in claim 15, in which the step b. obtaining of at least one multi-dimensional data set(s) comprising intensity as a function of wavelength and a function of a plurality of discrete settings of said at least one means for discretely, sequentially, modifying a polarization state of a beam of electromagnetic radiation provided by said source of polychromatic electromagnetic radiation for each of at least two ellipsometrically distinguished sample systems, involves obtaining data from at least as many sample systems as are utilized discrete settings of said at least one means for discretely, sequentially, modifying a polarization state of a beam of electromagnetic radiation provided by said source of polychromatic electromagnetic radiation.

17. A method of calibrating a spectroscopic ellipsometer system as in claim 15, in which the step of providing a spectroscopic ellipsometer system further comprises providing a reflectometer in a combination with the ellipsometer system, said combination comprising a spectroscopic reflectometer/ellipsometer system being configured such that a polychromatic beam of electromagnetic radiation provided by said source of polychromatic electromagnetic radiation can be directed to interact with a sample system present on said stage for supporting a sample system without any polarization state being imposed thereupon; and such that a polychromatic beam of electromagnetic radiation provided by said source of polychromatic electromagnetic radiation can be, optionally simultaneously, directed to interact with a sample system present on said stage for supporting a sample system after a polarization state has been imposed thereupon.

18. A method of calibrating a spectroscopic ellipsometer system as in claim 17 in which the step of providing a polychromatic beam of electromagnetic radiation without any polarization state being imposed thereupon which is directed to interact with a sample system present on said stage for supporting a sample system, is caused to approach said sample system at a near normal angle-of-incidence; and wherein a polychromatic beam of electromagnetic radiation provided by said source of polychromatic electromagnetic radiation upon which a polarization state has been imposed, is directed to interact with a sample system present on said stage for supporting a sample system at an angle near the Brewster angle of the sample system.

19. A method of calibrating a spectroscopic ellipsometer system as in claim 18, in which at least one of said polychromatic beam of electromagnetic radiation provided by said source of polychromatic electromagnetic radiation upon which is, or is not, imposed a polarization state, is directed to interact with a sample system present on said stage for supporting a sample system via a fiber optic means.

20. A method of calibrating a spectroscopic ellipsometer system as in claim 15, in which the step of providing a polychromatic beam of electromagnetic radiation comprises providing an output beam of polychromatic electromagnetic radiation which has a relatively broad and flattened intensity vs. wavelength characteristic over a wavelength spectrum for use in said present invention systems, said output beam of polychromatic electromagnetic radiation substantially be a comingled composite of a plurality of input beams of polychromatic electromagnetic radiation which individually do not provide as relatively broad and flattened a intensity vs. wavelength characteristic over said wavelength spectrum, as does said output comingled composite beam of polychromatic electromagnetic radiation, said system for providing an output beam of polychromatic electromagnetic radiation which has a relatively broad and flattened intensity vs. wavelength characteristic over a wavelength spectrum comprising:

a. at least a first and a second source of polychromatic electromagnetic radiation; and b. at least a first electromagnetic beam combining means;

said at least a first electromagnetic beam combining means being positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

21. A spectroscopic ellipsometer system comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system;
said spectroscopic ellipsometer system further comprising at least one means for discretely, sequentially, modifying a polarization state of a beam of electromagnetic radiation provided by said source of polychromatic electromagnetic radiation through a plurality of polarization states, said means for discretely, sequentially, modifying a polarization state of a beam of electromagnetic radiation provided by said source of polychromatic electromagnetic radiation through a plurality of polarization state being present at at least one location selected from the group consisting of:

between said polarizer and said stage for supporting a sample system; and between said stage for supporting a sample system and said analyzer;

and positioned so that said beam of electromagnetic radiation transmits therethrough in use;

in which said at least one means for discretely, sequentially, modifying a polarization state of a beam of electromagnetic radiation provided by said source of polychromatic electromagnetic radiation through a plurality of polarization states, is at least one rotatable compensator that changes the phase angle between orthogonal components of said electromagnetic beam of radiation provided by said source of polychromatic electromagnetic radiation; and in which said source of polychromatic electromagnetic radiation comprises an output beam of polychromatic electromagnetic radiation which has a relatively broad and flattened intensity vs. wavelength characteristic over a wavelength spectrum for use in said present invention systems, provides that said output beam of polychromatic electromagnetic radiation substantially be a comingled composite of a plurality of input beams of polychromatic electromagnetic radiation which individually do not provide as relatively broad and flattened a intensity vs. wavelength characteristic over said wavelength spectrum, as does said output comingled composite beam of polychromatic electromagnetic radiation, said system for providing an output beam of polychromatic electromagnetic radiation which has a relatively broad and flattened intensity vs. wavelength characteristic over a wavelength spectrum comprising:

a. at least a first and a second source of polychromatic electromagnetic radiation; and b. at least a first electromagnetic beam combining means;

said at least a first electromagnetic beam combining means being positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

* * * * *